(12) United States Patent
Herbst et al.

(10) Patent No.: US 12,070,229 B1
(45) Date of Patent: Aug. 27, 2024

(54) METHOD, DEVICE, AND NETWORK FOR STOPPING BLOOD LOSS

(71) Applicant: GOLDEN HOUR MEDICAL, LLC, Boca Raton, FL (US)

(72) Inventors: Hannah Herbst, Boca Raton, FL (US); Devin Willis, Boca Raton, FL (US)

(73) Assignee: Golden Hour Medical, Inc., Boca Raton, FL (US)

( * ) Notice: Subject to any disclaimer, the term of this patent is extended or adjusted under 35 U.S.C. 154(b) by 0 days.

(21) Appl. No.: 18/368,352

(22) Filed: Sep. 14, 2023

(51) Int. Cl.
*A61B 17/135* (2006.01)
*A61B 17/132* (2006.01)

(52) U.S. Cl.
CPC ...... *A61B 17/1355* (2013.01); *A61B 17/1325* (2013.01)

(58) Field of Classification Search
CPC . A61B 17/132; A61B 17/1322; A61B 17/135; A61B 17/1355
See application file for complete search history.

(56) References Cited

U.S. PATENT DOCUMENTS

| | | | |
|---|---|---|---|
| 7,479,154 B2 | 1/2009 | McEwen et al. | |
| 7,947,061 B1 | 5/2011 | Reis | |
| 10,136,900 B2 | 11/2018 | Menashe | |
| 10,758,247 B1 | 9/2020 | McEwen et al. | |
| 11,138,855 B2 | 10/2021 | Jafri et al. | |
| 2009/0030365 A1 | 1/2009 | Tokumoto et al. | |
| 2012/0046546 A1* | 2/2012 | Strobl | A61M 5/16854 600/431 |
| 2014/0266718 A1* | 9/2014 | Bongberg | A61N 1/3904 340/540 |
| 2015/0190301 A1 | 7/2015 | Leschinsky | |
| 2016/0008005 A1 | 1/2016 | McEwen et al. | |
| 2016/0310149 A1* | 10/2016 | Downey | A61B 5/02233 |
| 2017/0312165 A1 | 11/2017 | Johnson et al. | |
| 2018/0014832 A1* | 1/2018 | Lampropoulos | A61B 17/1355 |
| 2018/0193029 A1* | 7/2018 | McEwen | A61B 90/90 |

(Continued)

FOREIGN PATENT DOCUMENTS

WO   WO 2021/041006   *   4/2021

OTHER PUBLICATIONS

A New Method for Estimating Arterial Occlusion Pressure in Optimizing Pneumatic Tourniquet Inflation Pressure. Bahattin Tuncali, MD., et al. Anesth Analg 2006:102:1752-7.

(Continued)

*Primary Examiner* — Elizabeth Houston
*Assistant Examiner* — Lindsey Bachman
(74) *Attorney, Agent, or Firm* — Weisberg I.P. Law, P.A.

(57) ABSTRACT

A networking-capable emergency tourniquet including an adjustable and inflatable cuff configured to encircle a limb of a patient, and a controller unit removably coupled to the inflatable cuff. The controller unit includes a microcontroller configured to control the introduction, removal, and maintenance of air within the inflatable cuff and process collected patient data, a communicator unit configured to communicate with the user, a transmitter configured to transmit the collected patient data to a centralized server over a communication network, and a receiver configured to receive information from at least one of the centralized server and other sources over the communication network.

7 Claims, 23 Drawing Sheets

(56) References Cited

U.S. PATENT DOCUMENTS

| | | | |
|---|---|---|---|
| 2020/0237606 A1 | 7/2020 | Colosi | |
| 2020/0360027 A1* | 11/2020 | Marcus | A61H 9/0092 |
| 2021/0251500 A1* | 8/2021 | Vasandani | A61B 17/1355 |
| 2022/0003347 A1 | 1/2022 | Barthel et al. | |
| 2022/0346717 A1* | 11/2022 | Nguyen | A61B 17/1322 |
| 2023/0038923 A1* | 2/2023 | Le Blanc | A61B 17/1322 |

OTHER PUBLICATIONS

Tourniquet Cuff Pressure The Gulf Between Science and Practice. Nirmal C. Tejwani, MD. et al. The Journal of Trauma, vol. 61, No. 6, Dec. 2006.

Prolonged Care To Demonstrate a Medicated Combat Tourniquet Capable of Wound Infection Treatment Delivery. Department of Defense, Feb. 10, 2022.

Noninvasive Multimodal Imaging to Predict Recovery of Locomotion After Extended Limb Ischemia. Jason S. Randowsky, et al. Plos One DOI:10.1371. Sep. 14, 2015.

Persistent Microcirculatory Alterations are Associated With Organ Failure and Death in Patients With Septic Shock. Yasser Sakr, MB, BCh, MSh, Marc., et al. Crit Care Med 2004, vol. 32, No. 9.

Hemorrhagic Shock. S.W. Lee, et al. The New England Journal of Medicine. DOI: 10.1056/ NEJMc1802361.

States Require Schools to Have AEDs & Bleeding Control Kits. Aed Blog Jul. 6, 2020.

Early Antibiotics and Debridement Independently Reduce Infection in an Open Fracture Model. J.G. Penn-Barwell, et al. The Journal of Bone & Joint Surgery, vol. 94-B, No. 1, Jan. 2012.

Type III Open Tibia Fractures: Immediate Antibiotic Prophylaxis Minimizes Infection. William D. Lack, MD. et al. J Ortho Trauma, vol. 29, No. 1, Jan. 2015.

Infection Prevention in Combat-Related Injuries. LCDR Omar Saeed, MC, USN., et al. Military Medicine, 183, 9/10:137, 2018.

Extended (16-Hour) Tourniquet Application After Combat Wounds: A Case Report and Review of the Current Literature. John F. Kragh, et al. J Orthop Trauma, vol. 21, No. 4, Apr. 2007.

The Use of Lower Tourniquet Inflation Pressure in Extremity Surgery Facilitated by Curved and Wide Tourniquet and an Integrated Cuff Inflation System. R.A. Pedowitz, et al. Clin Orthop Relat Res. Feb. 1993;(287):537-44.

Defining The Optimal Time to the Operating Room May Salvage Early Trauma Deaths. Kyle N. Remick, MD. et al. Trauma Acute Care Surg, vol. 76. No. 5, Feb. 2014.

Preliminary Comparison of Pneumatic Models of Tourniquet for Prehospital Control of Limb Bleeding in a Manikin Model. Rudy Gibson, et al. J Spec Oper Med. 2016 Summer;16(2):21-7.

Evaluation of Models of Pneumatic Tourniquet in Simulated Out-of-Hospital Use. John F. Kragh Jr., et al. J Spec Oper Med. 2016 Fall;16(3):21-29.

The Tourniquet Gap A Pilot Study of the Intuitive Placement of Three Tourniquet Types by Laypersons. Elliot M. Ross, MD, MPH., et al. The Journal of Emergency Medicine, vol. 54, No. 3, pp. 307-314, 2018.

A 3D-Printed Microfluidic-Enabled Hollow Microneedle Architecture for Transdermal Drug Delivery, Biomicrofluidics 13, 064125 (2019).

Development of Adaptive Pneumatic Tourniquet Systems Based on Minimal Inflation Pressure for Upper Limb Surgeries. Hong-yun Liu et al. BioMedical Engineering 2013.

Implementation of Portable Automatic Tourniquet with High-Elasticity Biocompatible Strap. Seong Tak Woo et al. Appl. Sci. 2021.

Automatic Tourniquet System for Military Emergencies—Marina Felt et al. California Polytechnic State University BMED 455/456 (2021).

Surgical Tourniquet Technology Adapted for Military and Prehospital Use. James A. McEwen et al. MP-HFM-109-P-19.

Auto-Transfusion Tourniquets the Next Evolution of Tourniquets. David H Tang et al. Dovepress.

Development and Characterization of a Self-Tightening Tourniquet System. Saul J. Vega et al. Sensors 2022.

The Best Tourniquet System Personalized Tourniquet System. J.A. McEwen. Tourniquets.org.

Smart Tourniquet System for Military Use. Erdem Budak et al. IFMBE Proceedings Book (2018).

Intelligent Tourniquet System for Emergency Aid Using Wireless Network. Dr. K. S. Dhanalakshmi et al. ISSN 2456-2165 vol. 5 Issue 9, Sep. 2020.

An Intelligent Tourniquet System to Stop Traumatic Extremity Bleeding. John F. Kragh Jr. MD et al. The American Journal of Emergency Medicine, Nov. 2014.

Intelligent Tourniquet System for Emergency Aid. Faruk Beytar et al.

Low-Cost and Cleanroom-Free Fabrication of Microneedles. Hojatollah Rezaei Nejad et al. Microsystems & Nanoengineering (2018).

Spray-Formed Layered Polymer Microneedles for Controlled Biphasic Drug Delivery. Seok Chan Park et al. Polymers 2019,11,369.

Microneedles: A Smart Approach and Increasing Potential for Transdermal Drug Delivery System. Tejashree Waghule et al. Biomedicine & Pharmacotheraphy 109 (2019) 1249-1258.

Outpatient Subcutaneous Antimicrobial Therapy (OSCAT) as a Measure to Improve the Quality and Efficiency of Healthcare Delivery for Patients With Serious Bacterial Infections. Tristan Ferry et al. Frontiers in Medicine vol. 7, Article 585658, Dec. 2020.

Tactical Combat Casualty Care: Lessons and Best Practices. CALL Handbook No. 17-13. Version 5. May 2017.

Efficacy of Prehospital Application of Tourniquets and Hemostatic Dressing to Control Traumatic External Hemorrhage. Emerging Issues in EMS and 911. U.S. Department of Transportation. May 2014.

Guidelines for Best Practices for Safety Use of Pneumatic Tourniquets. AST (Association of Surgical Technologies (2007).

Design of a Thermaly Controlled System for Medications. Kishan Narotam. Oct. 25, 2019.

Engineering Microneedle Patches for Improved Penetration: Analysis, Skin Models and Factors Affecting Needle Insertion. Pooyan Makvandi et al.—ISSN 2311-6706 (2021).

A Review of Shape Memory Allow Research, Applications and Opportunities. Jaronie Mohd Jani et al. Materials and Design 56 (2014) 1078-1113.

Tourniquets Exposed to the Afghanistan Combat Environment Have Decreased Efficacy and Increased Breakage Compared to Unexposed Tourniquets—LCDR Richard Childers, MC USN, et al. Military Medicine, 176, 12:1400, 2011.

A Systematic Review of the Relationship Between Blood Loss and Clinical Signs. Rodolfo Carvalho, et al. Plos One, vol. 8 Issue 3, e57594. Mar. 2013.

The Value of Traditional Vital Signs, Shock Index, and Age-Based Markers in Predicting Trauma Mortality. Stevan R. Bruijns, FCEM, et al. 2013 Lippincott Williams & Wilkins.

Battlefield Tourniquets: Lessons Learned in Moving Current Care Toward Best Care in an Army Medical Department at War. Kragh, John F., et al. U.S. Army Medical Department Journal. Apr. 1, 2016.

Plasma Flow Distal to Tourniquet Placement Provides a Physiological Mechanism for Tissue Salvage. Emily Busse, et al. Plos One, Dec. 21, 2020.

Tourniquets and Occlusion: The Pressure of Design. Piper L. Wall, DVM, PhD, et al. Military Medicine, 178, 5:578, 2013.

Occlusion of Arterial Flow in the Extremities at Subsystolic Pressures Through the Use of Wide Tourniquet Cuffs. Brent Graham, MD, FRCSC, et al. Clinical Orthopedics and Related Research, No. 283. Jan. 1993.

Duration of Extremity Tourniquet Application Profoundly Impacts Soft-Tissue Antibiotics Exposure in a Rat Model of Ischemia-Reperfusion Injury. Lee C. Mangum, et al. Injury 50 (2019) 2203-2214.

Prolonged Tactical Tourniquet Application for Extremity Combat Injuries During War Against Terrorism in the Sahelian Strip. Alexandre Sabate-Ferris, et al. European Journal of Trauma and Emergency Surgery (2022) 48:3847-3854.

Minor Morbidity With Emergency Tourniquet Use to Stop Bleeding in Severe Limb Trauma: Research, History, and Reconciling Advo-

(56) References Cited

OTHER PUBLICATIONS cated and Abolitionist. COL John F. Kragh Jr., MC USA, et al. Military Medicine, 176, 7:817, 2011.

Tourniquet Use is Not Associated With Limb Loss Following Military Lower Extremity Arterial Trauma. David S. Kauvar, MD. et al. Trauma Acute Care Surg. vol. 85, No. 3 (2018).

An Evaluation of Two Tourniquet Systems for the Control of Prehospital Lower Limb Hemorrhage. David M. Taylor, MBChB et al. The Journal of Trauma vol. 71, No. 3, Sep. 2011.

Evaluation of Possible Tourniquet Systems for Use in the Canadian Forces. Roger B. King, CCFP. et al. The Journal of Trauma, vol. 60, No. 5, May 2006.

Physiological Evaluation of the U.S. Army One-Handed Tourniquet. Joseph C. Wenke, PhD. et al. Military Medicine, 170, 9:776, 2005.

Tourniquets in Orthopedic Surgery. Jai Prakash Sharma, et al. Indian Journal of Orthopedics 2012 46(4): 377-383.

The Military Emergency Tourniquet Program's Lessons Learned With Devices and Designs. COL John F. Kragh Jr., MC USA. et al. Military Medicine, 176, 10:1144, 2011.

The Safety of the Esmarch Tourniquet. W. C. Biehl 3rd. et al. Jun. 14, 1993(5):278-83.

Practical Use of Emergency Tourniquets to Stop Bleeding in Major Limb Trauma. John F. Kragh, Jr., MD. et al. The Journal of Trauma, vol. 64, No. 2, Feb. Supplement 2008.

"Stop the Bleeding": A U.S. Military Installation's Model for Implementation of a Rapid Hemorrhage Control Program. COL James Alan Chambers, USAF, MC , SFS. et al. Military Medicine, 187, 3/4:67. 2019.

Pneumatic Tourniquets in Extremity Surgery. Abel Wakai, MB et al. Journal of the American Academy of Orthopaedic Surgeons. vol. 9, No. 5 Sep./Oct. 2001.

Tourniquet Application During Anesthesia: "What We Need to Know?". Kamal Kumar, et al. 2016 Journal of Anesthesiology Clinical Pharmacology.

Anatomical Changes in Peripheral Nerves Compressed By A Pneumatic Tourniquet. J. Ochoa, et al. J. Anat. (1972) 113,3, pp. 433-455.

The Use of Lower Tourniquet Inflation Pressures in Extremity Surgery Facilitated by Curved and Wide Tourniquets and Integrated Cuff Inflation System. Robert A. Pedowitz, MD., PhD. et al. Clinical Orthopedics and Related Search, No. 287, Feb. 1993.

What is a Tourniquet "Limb Occlusion Pressure" (LOP). J.A. McEwen. Tourniquets.org.

Survival With Emergency Tourniquet Use to Stop Bleeding in Major Limb Trauma. COL John F. Kragh, Jr. MC, USA. et al. Annals of Surgery, vol. 249, No. 1, Jan. 2009.

The Windlass Tourniquet: Is It Taking the Wind Our of the "Stop the Bleed" Sails ?. Victoria L. Schlanser, DO, MS, FACS, FACOS, et al. Journal of Surgical Research, Mar. 2022 (271) 91-97.

Can We Stop the Bleed? Evaluation of Tourniquet Application by Individuals With Varying Levels of Prior Self-Reported Training. Justin C. McCarty, et al. Injury, Int. J. Care Injured 50 (2019) 10-15.

Complications Associated with Prolonged Tourniquet Application on the Battlefield. Lior Dayan, MD., et al. Military Medicine, 173, 1:63-66, 2008.

\* cited by examiner

METHOD, DEVICE, AND NETWORK FOR STOPPING BLOOD LOSS

TECHNICAL FIELD

The present disclosure relates to tourniquets and more specifically to a system and method for rapidly treating patients following traumatic injury by use of at least one automated pneumatic emergency tourniquet, where the tourniquet is configured to transmit data to a network.

BACKGROUND OF THE INVENTION

Rapid access to tourniquets is critical to stop extremity bleeding and prevent morbidity and mortality. Depending on the location of the bleed and severity of the injury, hemorrhage can become life-threatening in seconds. Windlass tourniquets are conducive to neither speed nor accuracy, which are critical to save a life in emergency scenarios. Studies indicate that slow response time, improper placement, and inadequate tightness are significant factors contributing to the failure of windlass tourniquets in controlling bleeding.

The increase in survival rate made possible by early hemorrhage control is enhanced when paramedics and responders can arrive on the scene quickly. There are over 2 million people trained to stop extremity hemorrhage, but if they are not aware of a nearby extremity hemorrhage occurring they are unable to be of assistance. Thus the most effective way to control hemorrhage is to dispatch the closest tourniquet to the bleed site and to effectively apply it to the limb. Prior art systems describe locators for Automatic External Defibrillators (AEDs), however, AEDs are helpful for treating cardiac arrest, not exsanguinating hemorrhage. Other systems describe location systems for emergency devices such as fire extinguishers, however this is helpful for extinguishing a fire, not for stopping extremity bleeding. Thus a need exists to deliver rapid care to stop emergency bleeding.

Inadequate tightness is a limitation of windlass tourniquets. Pneumatic electronic tourniquets of the prior art overcome some of the problems with windlass tourniquets, however they are nearly exclusively intended for surgical settings. Prior art systems describe automated pneumatic tourniquets for surgical purposes that provide real-time pressure data and can be adjusted, however they are usually heavy and are not practical for portability. Additionally, the inflatable cuffs designed to be compatible with these systems can cost hundreds of dollars per unit, and the inflation units can cost thousands of dollars. For emergency scenarios, where tourniquets likely become contaminated with bodily fluids or biohazardous materials, it is pivotal that cuffs are disposable and systems are economically feasible, which is a further limiting factor in prior art systems. In other prior art systems, inflation mechanisms and cuffs are described as integral to one another, or have underdeveloped attachment and detachment mechanisms for rapid setup, deployment, and deconstruction. This is not conducive to the speed and access necessary for emergency scenarios. The proper placement and inflation of the tourniquet requires medical credentials and extensive training, making it challenging for non-specialists or first responders to utilize effectively. Additionally, maintaining the necessary air pressure and monitoring the tourniquet's duration during extended field operations can be cumbersome and impractical. Moreover, the risk of potential complications, such as nerve or tissue damage, increases when skilled medical supervision and precise control are lacking. Considering these factors, pneumatic tourniquets have been limited in their ability to be deployed for emergency use.

Other documents describe a limb occlusion device that has a dual-cuff system. One cuff is to be held at a high enough pressure to stop the flow of blood through the limb, while the other is to recognize the presence of an arterial blood flow through oscillations. Although a mentioned application is toward emergency use in the field, consideration is not given to limitations of using the device in the field: patient movement is virtually guaranteed following the onset of a tourniquet application which makes accurate oscillatory blood pressure measurement highly impractical, therefore the basis for tightening above a limb occlusion pressure is erroneous. A single battery may not be adequate to power the device for an entire application cycle, especially for prolonged care scenarios where application time can exceed 72 hours, and consideration is not given to the type of battery which may be impacted by extreme temperatures.

Improper placement presents an additional limitation when it comes to tourniquet usage. Research demonstrates that tourniquets should not be positioned over joints and are unsuitable for limbs with multiple bones, such as the forearm. In high-stress situations, it is critical to remind users, particularly those with minimal or no training, about these guidelines. Traditional windlass tourniquets and automated tourniquets from previous designs often rely on physical instruction manuals or device labeling, which are inconvenient to carry with the device and unlikely to be consulted during a rapidly evolving emergency. Consequently, the absence of clear instructions contributes to higher failure rates when applying conventional tourniquets.

Some prior art documents suggest applications for implementing pneumatic tourniquets into the field without consideration to how this would practically work. For example, the need for tourniquet availability in public settings is clear due to shootings and mass casualty events in locations such as schools, stadiums, offices, and stores, however prior art systems do not describe an effective storage solution for battery powered or rechargeable devices. Additionally, electronic use is described, but consideration is not given to how tourniquet systems will communicate with responders, physicians or other medical personnel. Furthermore, documents fail to describe a practical monitoring solution for a plurality of automatic tourniquets, leaving readers under the assumption that each automatic tourniquet would require manual battery or systems checks, which are time consuming and impractical.

Thus a need exists to overcome the aforementioned problems with the prior art.

SUMMARY OF THE INVENTION

The present disclosure provides a system and method for rapidly treating patients following traumatic injury. In one embodiment of the present disclosure, a networking-capable emergency tourniquet is provided. The tourniquet includes an adjustable and inflatable cuff configured to encircle a limb of a patient, and a controller unit removably coupled to the inflatable cuff. The controller unit includes a microcontroller configured to control the introduction, removal, and maintenance of air within the inflatable cuff and interpret patient data, a communicator unit configured to communicate with a user, a transmitter configured to transmit the collected patient data to a centralized server over a communication network, and a receiver configured to receive information from at least one of the centralized server and other sources over the communication network. In some embodiments, the information from the centralized server includes at least one of visual and audible instructions to a user of the tourniquet, which may be delivered through at least one of a speaker or visual display. The centralized server may be in communication with a plurality of network-capable emergency tourniquets. In some embodiments this tourniquet weights less than eighteen pounds and is therefore ideal for portability. The communicator unit may transmit collected patient data upon activation of the controller, such as in one embodiment the location of the tourniquet and the patient. Patient data may also include elapsed application time, patient blood pressure, tourniquet pressure, or other metrics that may be helpful to treatment. In some embodiments a request for assistance is communicated to an emergency dispatcher through the communicator. The tourniquet may include an RFID tag, which may be configured to store information specific for each tourniquet.

In one embodiment, the network-capable emergency tourniquets may be stored in a tourniquet storage station. The tourniquet storage station comprises in one embodiment at least one network-capable emergency tourniquet, a station controller configured to aggregate data received from the tourniquet or multiple tourniquets, an internet access point allowing the aggregated data to be accessed via the internet, a transmitter configured to transmit the aggregated data to a centralized server. In some embodiments the station may include a locator configured to report the location of the tourniquet station to the centralized server or to a user. In some embodiments the storage station includes at least one charger to charge each of the network-capable emergency tourniquets. The charger may include an RFID tag that allows an external device to receive and display status and troubleshoot connectivity issues. The storage station may also include mechanical inflators.

The network-capable emergency tourniquet may be utilized to aid a patient. In one method of use, the tourniquet is programmed with a location. Upon activation of the tourniquet, the network receives the status of the tourniquet, and transmits the location of the patient to at least one of a remote emergency dispatcher and a first responder located within a predetermined distance of the location of the patient. If the tourniquet is moved, the location of the patient is updated, and at least one of the remote emergency dispatchers and first responders is given the updated location of the patient. In one embodiment, the method comprises at least one of verbal instructions and visual instructions being delivered. The location information can be further specified to include the floor and room number indicating where the tourniquet is stored.

In one method of utilizing the tourniquet, a centralized server is notified of the patient emergency bleeding situation. The centralized server then identifies at least one tourniquet located in the proximity of the location of the patient emergency bleeding situation, wherein the at least one tourniquet is programmed with location information. A request for assistance is then delivered by the centralized server for the location of the patient emergency bleeding situation. Instructions may be delivered through a speaker to a user explaining how to deploy and operate the tourniquet. Further, the centralized server may deliver a notification to an emergency service to be deployed to the location of the emergency bleeding situation.

BRIEF DESCRIPTION OF THE DRAWINGS

The present disclosure will now be described, for exemplary purposes, in more detail by way of embodiment(s) and with reference to the enclosed drawings, in which.

DETAILED DESCRIPTION

In the following, in several scenarios, a detailed description is presented of the exemplary embodiments in conjunction with the accompanying drawings to enable easier understanding of the solution(s) described herein.

Figure 1A:
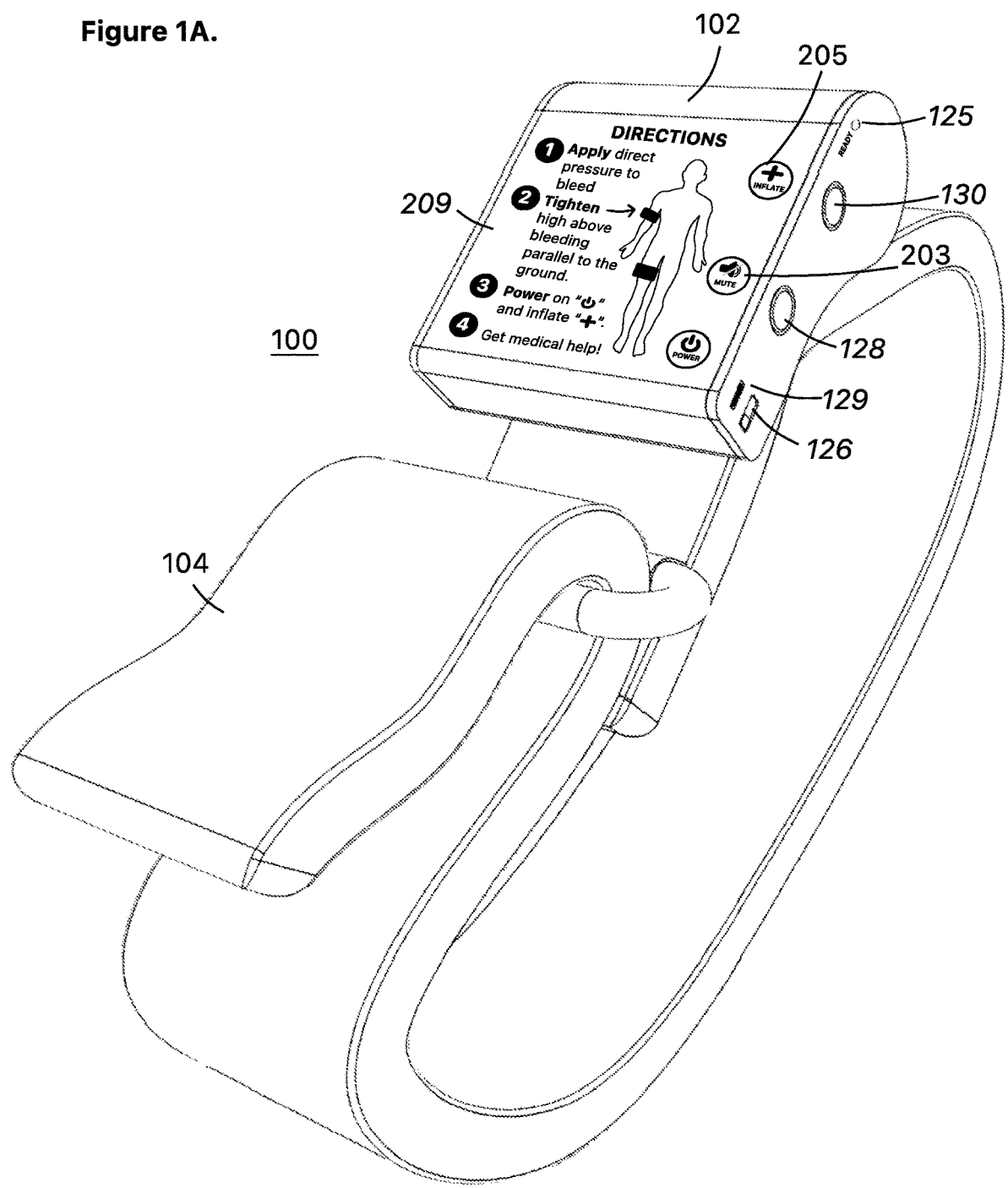
FIG. 1A shows an assembled tourniquet.
Figure 1B:
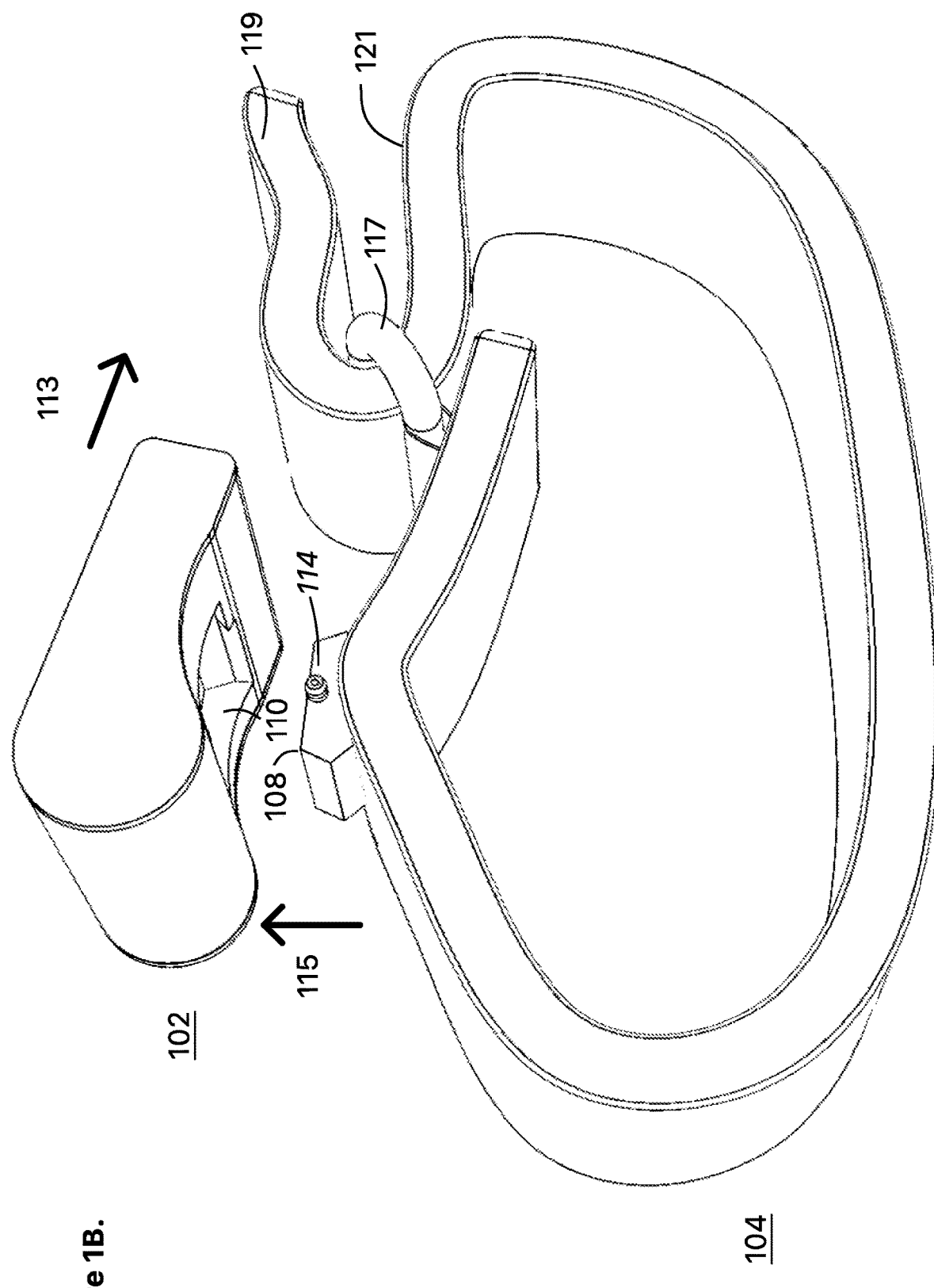
FIG. 1B shows the tourniquet separated into two components: the TQController and the TQCuff.

FIG. 1A provides a detailed view of the pneumatic tourniquet 100, which consists of two components shown separately in FIG. 1B: the TQController ("or "controller") 102 and the TQCuff (or "cuff") 104. The TQController 102 adds air into the TQCuff 104, which pressurizes the cuff when secured about a limb of a patient allowing it to slow and stop the bleeding.

The TQController 102 comprises a power switch 126 to power the tourniquet 100 on and off and a charging port 129. The power switch can be alternatively programmed to toggle between idle and active mode, rather than on and off mode in one embodiment. An LED indicator light 125 may be used to communicate readiness/non-readiness, battery life, etc., via a visual indication, such as, for example, color. Exemplary pictorial directions 209 are adhered to the top of the TQController 102 in some embodiments. In one non-limiting embodiment, they contain four steps to be completed in succession:
1. Apply direct pressure to bleed.
2. Tighten high above bleeding parallel to the ground.
3. Power on and inflate "+"
4. Get medical help!

In this embodiment, a series of controls, buttons, or switches are located on one or more sides of the TQController 102. There are two buttons in this embodiment. The "inflate" button 130 with corresponding label 205 controls the addition of air into the cuff 104 when prompted, which stops the bleed by applying pressure to compress the artery and the vein. In one embodiment, the tourniquet 100 includes a speaker that delivers audible instructions, which can be silenced by selecting the "mute" button 128 with corresponding label 203. It may be desirable to mute the audible instructions in some applications, such as, for example, in an active shooter situation or a military application. These audible instructions are explained in further detail below and with regard to FIG. 2E.

The controller 102 may comprise multiple buttons or controls with similar or different labeling, and the placement of controls may vary. Other examples of controls include, but are not limited to, those for contacting a dispatcher, decreasing pressure, or detaching the cuff 104 from the controller 102. Each of these can use universal symbols above or directly on the button. In certain embodiments, the control may comprise elements such as a depressible button, conductive button, switch, touch-sensitive interface, dial, or any combination thereof, configured to provide response input or command signals to the system. Alternatively, some or all controls may be removed in exchange for controls in a mobile application such as in FIG. 4E.

FIG. 1B shows the TQController 102 separated from the TQCuff 104. To secure the controller 102 onto the cuff 104, the cuff's integrated slider 108 is moved vertically into the TQController's receiver 110 in the direction of arrow 115. The components are securely positioned by bringing the cuff 104 and controller 102 towards each other until top valve 114 is securely in the TQController 102 following arrow 113. This integrates the top valve 114 with the TQController 102, allowing fluid access between the TQCuff's inflatable member 112 (shown in FIG. 1C) and the TQController's air pump 219 shown in FIGS. 2A-2B. The tourniquet 100 is fastened onto a limb by advancing the distal end of the TQCuff 104 through a loop 117, and securing it to the side of the cuff 104 which in some embodiments is lined with Hook and Loop 121. When directed, the TQController 102 then adds air into the TQCuff 104 to pressurize the tourniquet 100 and stop the bleed via arterial and venous compression. Cuff fabric 119 encases the inflatable member 112 embedded into the cuff 104 and is shown in more detail in FIG. 1C.

In certain embodiments, TQCuff 104 can be disposed of after each use to stop a bleed and replaced with a new cuff. This reduces the likelihood of pathogen transmission between patients. The TQCuff 104 can be manufactured in various widths and lengths, and tailored to accommodate limbs of different sizes. For instance, a narrower and shorter size is suitable for pediatric limbs, while a broader and longer size is better suited for adult limbs. These specifications can also be adjusted based on the specific limb type, such as a size customized for a pediatric patient's arm or an obese patient's leg. A Radio Frequency Identification (RFID) tag or similar identification means may be embedded into the cuff to store various cuff information, including the length, width, suitable inflation pressure, model number, lot number, serial number, production identifier, etc. Inclusion of an RFID tag would allow an RFID Reader incorporated into the TQController 102 to interpret the stored data and inflate the tourniquet faster and more effectively.

Figure 1C:
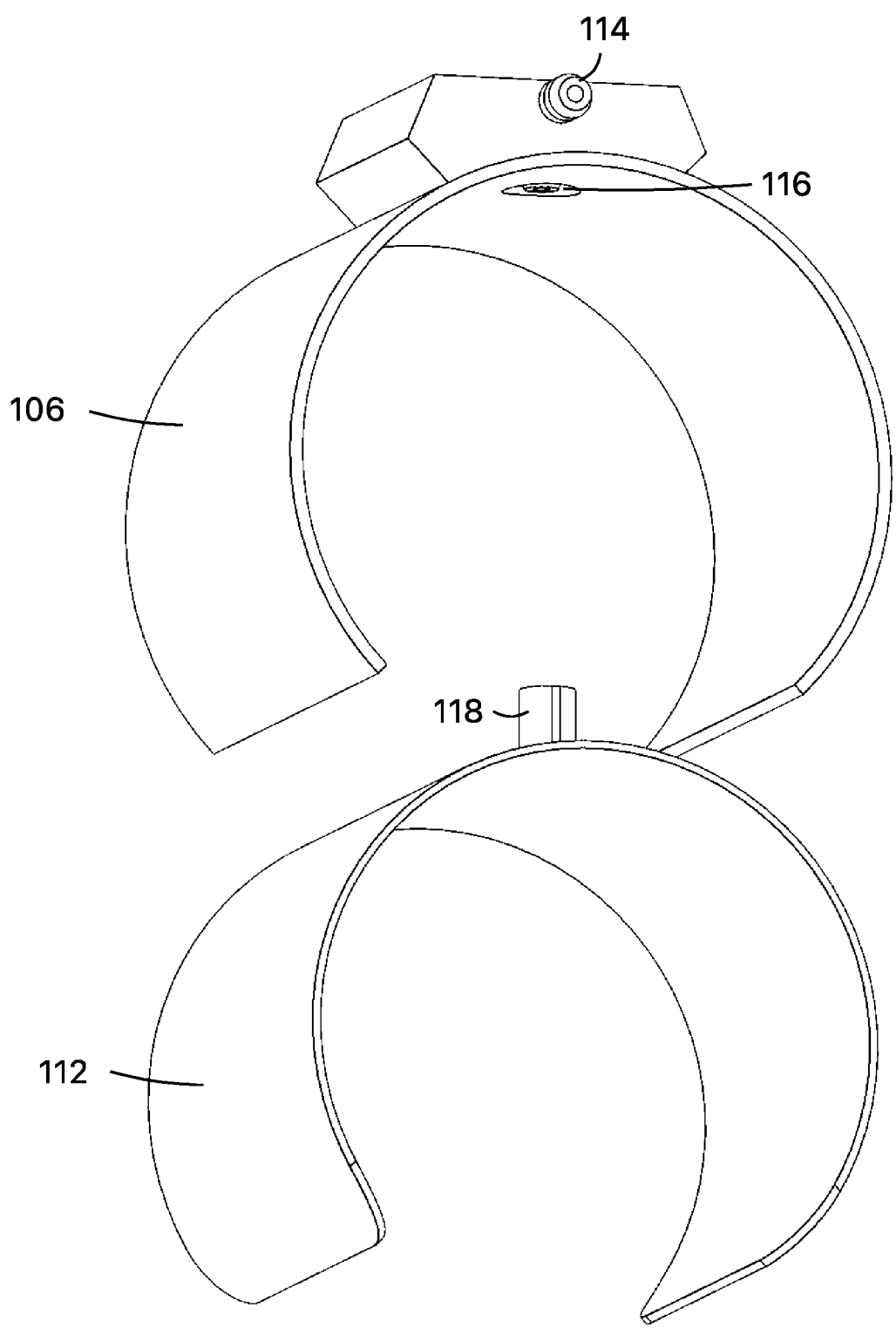
FIG. 1C shows the inside of a TQCuff.

An expanded view of the components of TQCuff 104 is shown in FIG. 1C. To achieve arterial and venous compression, the TQCuff 104 incorporates a limb conforming component 106 to facilitate rapid attachment to a limb. The limb conforming component 106 includes an integrated dual port air valve, comprising a top valve 114 and a bottom valve 116. In this embodiment, there is one bottom valve 116, but this can be replaced in favor of multiple bottom valves with multiple bladders as a fail-safe in case one bladder breaks. In some embodiments the valves can be one-way valves to prevent air leakage. Integrating both the top valve 114 and bottom valve 116 directly into the limb conforming component 106 minimizes the need for external components, reduces manufacturing time, and reduces the likelihood of breakage or faulty connections between components.

In one embodiment, TQController 102 housing and the limb conforming component 106 can be fabricated from stereolithography (SLA) printing with photopolymer resin. This manufacturing process ensures the creation of seamless and durable components. If resin is printed using SLA, the air valve hole may be cleared by first rinsing the print in Isopropyl Alcohol (IPA) as is standard procedure, then introducing air through the valve to clear out additional resin or IPA. Varying curing times with ultraviolet (UV) light to increase polymerization of the material post production allows for a higher degree of toughness and thus a longer product lifetime. Alternatively, these parts can also be fabricated through techniques such as injection molding, vacuum forming, powder printing, fused deposition modeling (FDM) 3D printing, or other suitable methods. The controller housing is constructed from a resilient material, allowing it to withstand repeated use. It is designed to be easily cleaned and sanitized for multiple applications. An exemplary cleaning method for the TQController 102 involves utilizing a bleach and water solution that is commonly employed in the sanitization and maintenance of reusable medical devices.

The inflatable member 112 is secured beneath the limb conforming component 106. The inflatable member's tubing 118 extends above the inflatable member 112 and is slid over the bottom valve 116.

Figure 1D:
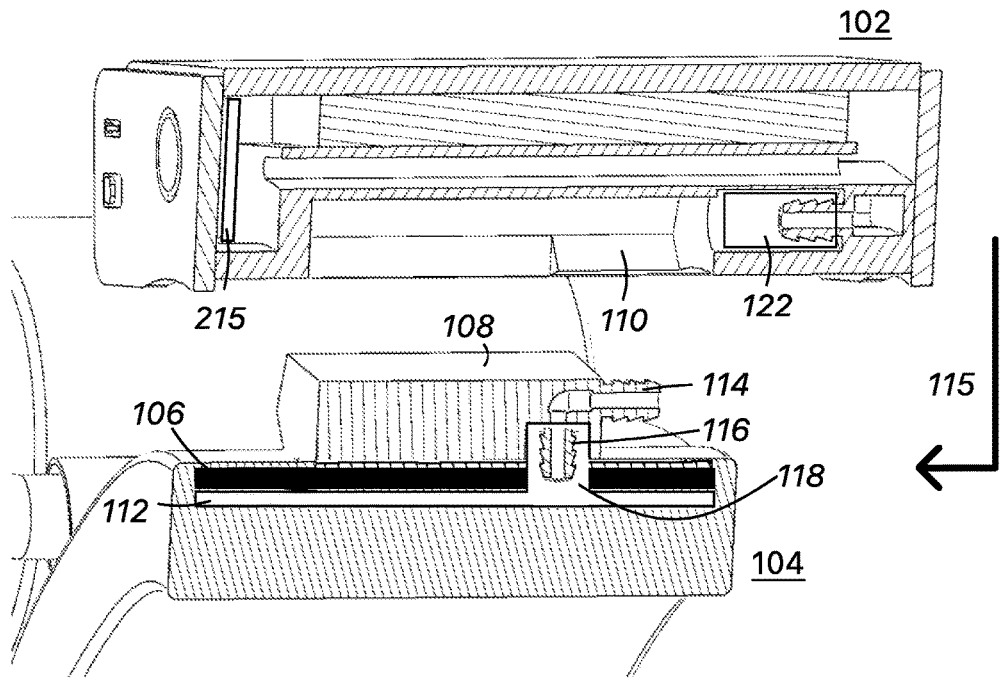
FIG. 1D shows a sectional view of the TQController interacting with the TQCuff prior to attachment.

FIG. 1D shows a cross sectional view of the TQCuff 104 and TQController 102 before attachment. During the manufacture of TQController 102, tubing is fastened inside guide 122, prior to use. The connection between tubing 118 and tubing stored in tubing guide 122 and the valves 114 and 116 is reliable due to the shape of the valves 114 and 116. An airtight seal is created because multiple inverted triangles of which the bases are slightly larger than tubing are integrated into the valves. This connection may be reinforced with an adhesive, silicone, cured resin, small zip tie, or other suitable fastener. A printed circuit board (PCB) 215 contains a microcontroller 210 that is responsible for controlling the circuitry 200, shown in detail in FIG. 2A. In certain embodiments, the microcontroller 210 is an ESP32 chip, possessing features such as wireless internet connectivity, Analog-to-Digital conversion (ADC), multiple sleep modes for reduced power consumption, and secure communication capabilities for establishing encrypted connections such as Transport Layer Security (TSL) connections. When connected to the internet, the device can utilize Voice Over Internet Protocol (VoIP) or real-time communication protocols to establish direct connections with emergency services. The microcontroller 210 facilitates data collection and records the time of tourniquet application, pressure levels, and other critical data.

The inflatable member 112 achieves connection with the controller 102 by the tubing 118 being fastened over valve 116. To set up a tourniquet 100 for use, connection between the TQCuff 104 and TQController 102 is mechanically achieved. In FIG. 1D, it can be seen that the slider 108 is integral to the limb conforming component 106. The slider 108 and receiver 110 guide the top valve 114 to enter the tubing 118 located within the tubing guide 122 when attached as indicated by arrow 115.

Figure 1E:
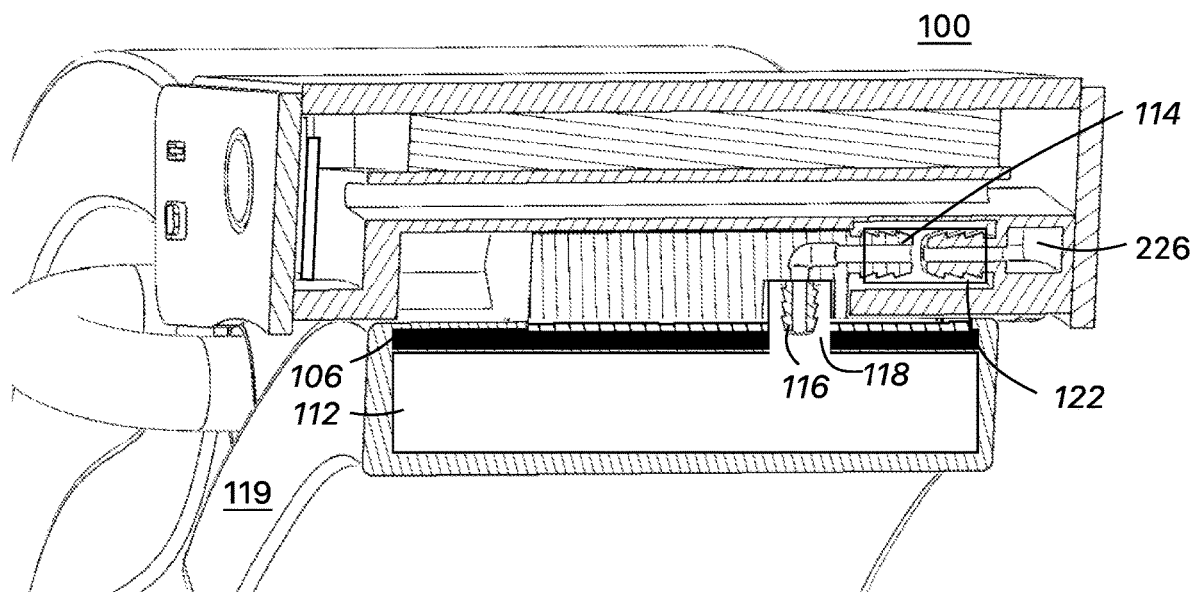
FIG. 1E shows a sectional view of the TQController interacting with the TQCuff after attachment.

FIG. 1E shows the result of the TQController 102 and TQCuff 104 being integrated from a cross section view. When selected, the "inflate" button 130 shown in FIG. 1A sends an "inflate" command through the microcontroller 210. The microcontroller 210 then directs the air pump 219 shown in FIGS. 2A-2B to release air to pressurize the inflatable member 112, which firstly travels through the air pathway 226, then through tubing guide 122, then bottom valve 116 and tubing 118, and finally causes the inflatable member 112 to inflate, which pressurizes the tourniquet cuff and reduces the flow of blood through the limb. Thus when the TQController 102 and the TQCuff 104 are attached, a fluid connection is formed that allows for stopping a bleed.

In some embodiments, the top valve 114 and tubing guide 122 are equipped with an attachment sensor, such as a colorimetric, capacitance, mechanical, or electrical touch sensor. This can provide an audible sound to indicate proper attachment during setup, or a visual indicator of proper attachment, such as a light change or other color change. The cuff 104 may further include a mechanical indicator when this attachment is achieved, indicating that the cuff 104 has been used and should not be re-used, such as a mechanical latch released to change a color indicator. Alternatively, the tourniquet 100 may conduct a pressure test by inflating the cuff's inflatable member 112 to determine if target pressure is achieved without the presence of a limb. If successfully inflated and pressure is maintained, it would follow that the connection is reliable. If the inflation test proves to be unsuccessful, an alert will be delivered from the centralized server 500 in FIG. 5 that the connection is unreliable. If this failure persists, further support will be necessary. This inflation test can be repeated at preset intervals, such as daily, to ensure that the components are ready for use. It is encouraged that attachment between the controller 102 and cuff 104 is secured prior to using the tourniquet 100 to facilitate speed when application is desired.

After using the tourniquet 100, the controller 102 and cuff 104 may be disengaged by guiding the slider 108 away from the receiver 110 by retracing the action demonstrated by arrow 115. This effectively terminates the connection between the cuff 104 and controller 102, facilitating the disposal of the cuff 104 and connection of a new cuff 104. Disposing the cuff 104 after use decreases the risk of infection or pathogen transmission between patients.

The dual valve system comprised of top valve 114 and bottom valve 116 may be designed to maintain pressure independent of the controller 102, so that the controller 102 can be used to inflate multiple cuffs 104 consecutively without needing constant attachment. This can be achieved by adding a check valve or one way direction to the integrated valves. This would allow the cuff 104 to operate independently of the controller 102, keeping pressure without constant regulation. This would be especially useful in a mass casualty incident where there are potentially a plurality of victims and a shortage of controllers 102. Additionally, this may save power during attachment, especially in the case of leakage from an electronic component where the system may compensate for air loss. Cuff fabric 119 is sewn around both the inflatable member 112 and the limb conforming component 106, preventing the inflatable member 112 and limb conforming 106 component from being detached during use.

Figure 1F:
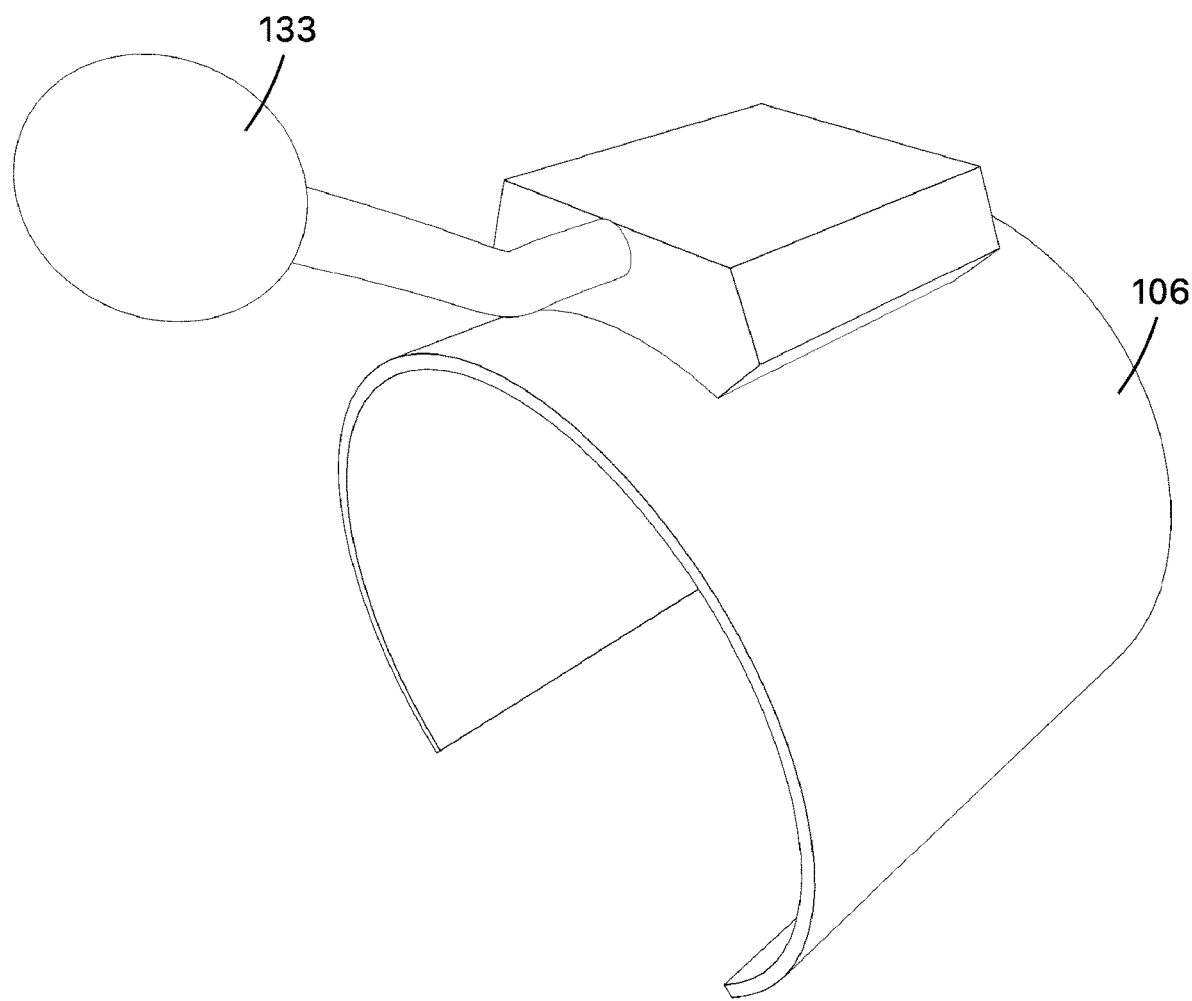
FIG. 1F shows a TQCuff inflated mechanically without the TQController.

In another embodiment shown in FIG. 1F, a mechanical bulb 133 may be attached to the top valve 114 on the limb conforming component 106 rather than the controller 102 for inflation. The bulb 133 must be repeatedly squeezed to add air to the inflatable member 112. This may be desirable for a military application where displacement of casualties makes charging or electronics difficult, or as a redundancy in the case of electronic failure. The bulb may be integrated with the electronics so pressure can still be monitored during use.

Figure 1G:
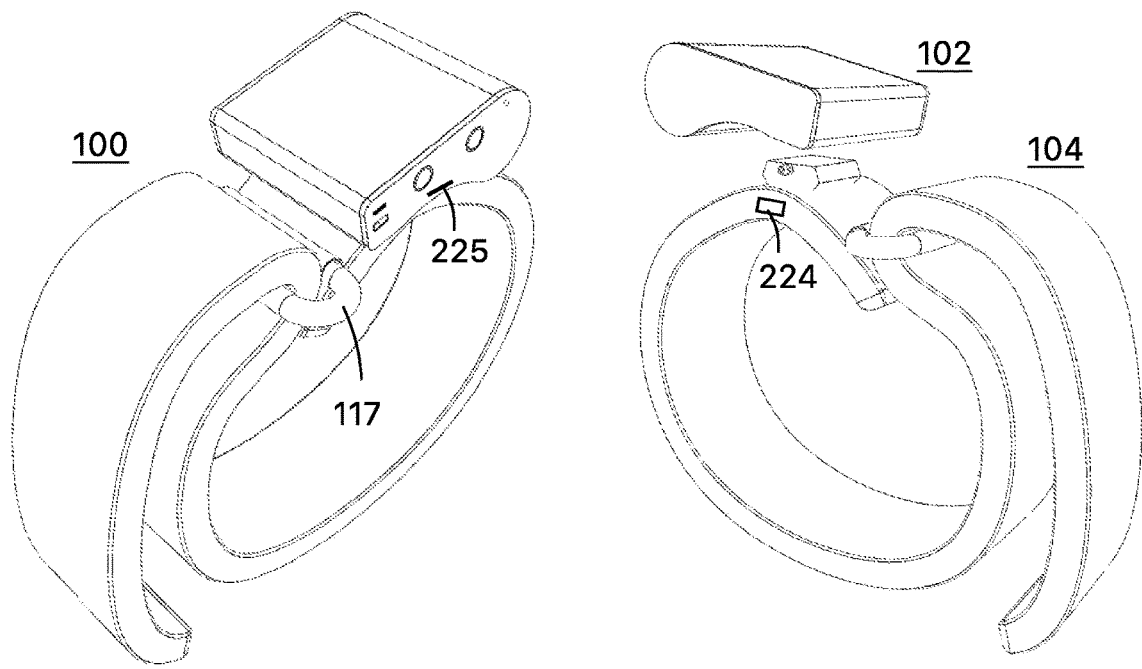
FIG. 1G shows an alternate TQCuff storage configuration and an embodiment where the TQController includes an RFID reader and tag.
Figure 1H:
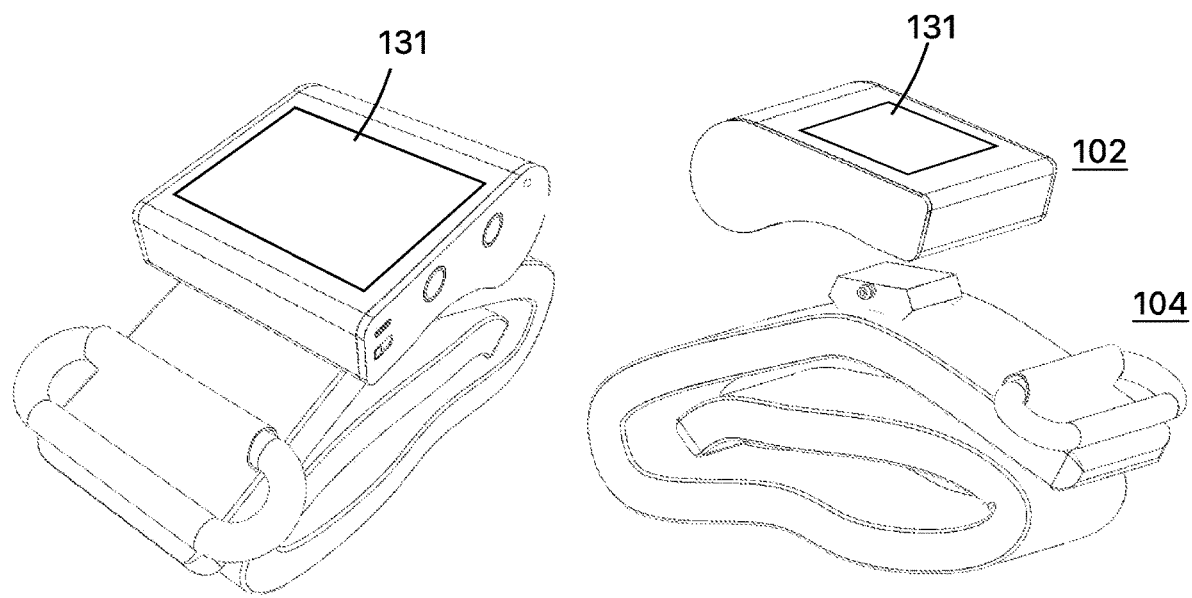
FIG. 1H shows an alternate TQCuff storage configuration and an embodiment where the TQController includes an LCD screen.

FIGS. 1G and 1H show alternative embodiments of the tourniquet 100. The cuff 104 may be stored in a "quick launch" configuration where it is secured through loop 117 and ready to be applied to a limb without full detachment. In some embodiments, both the TQCuff 104 and TQController 102 may incorporate RFID tags 224 or RFID readers 225. Here, the TQController 102 is shown having an RFID reader 225, and the TQCuff 104 is shown having an RFID tag 224. In other embodiments, TQController 102 includes RFID tag 224 and TQCuff 104 includes RFID reader 225. The RFID tags 224 securely hold fixed data such as, but not limited to, cuff length, ideal pressure, serial number, or others, ensuring accurate identification and tracking of the tourniquet. RFID tag 224 may be read by various devices, including but not limited to cell phones, controllers, TQStations such as in FIG. 3, or other compatible mechanisms. This fixed information is further accessible through the App shown in FIG. 4, or may be printed onto the device by a sticker or another label. RFID tag 224 or RFID tag reader 225 may be used to identify the tourniquet 100 easily within a TQStation shown in FIG. 3, for example, by scanning it upon entry.

FIG. 1H depicts the TQCuff 104 in a compact storage state. The TQController 102 incorporates an LCD Screen 131. LCD screen 131 can facilitate data presentation, encompassing time duration, exerted pressure, and comparative analysis between target and actual pressures to identify variances. In subsequent figures, the LCD screen 131 has capabilities to interface with emergency dispatch systems. Prior to operational use, LCD screen 131 can display battery status, software updates, version details, and other pertinent device information. Moreover, LCD screen 131 can serve a training function, offering live feedback on application precision during utilization.

Figure 1I:
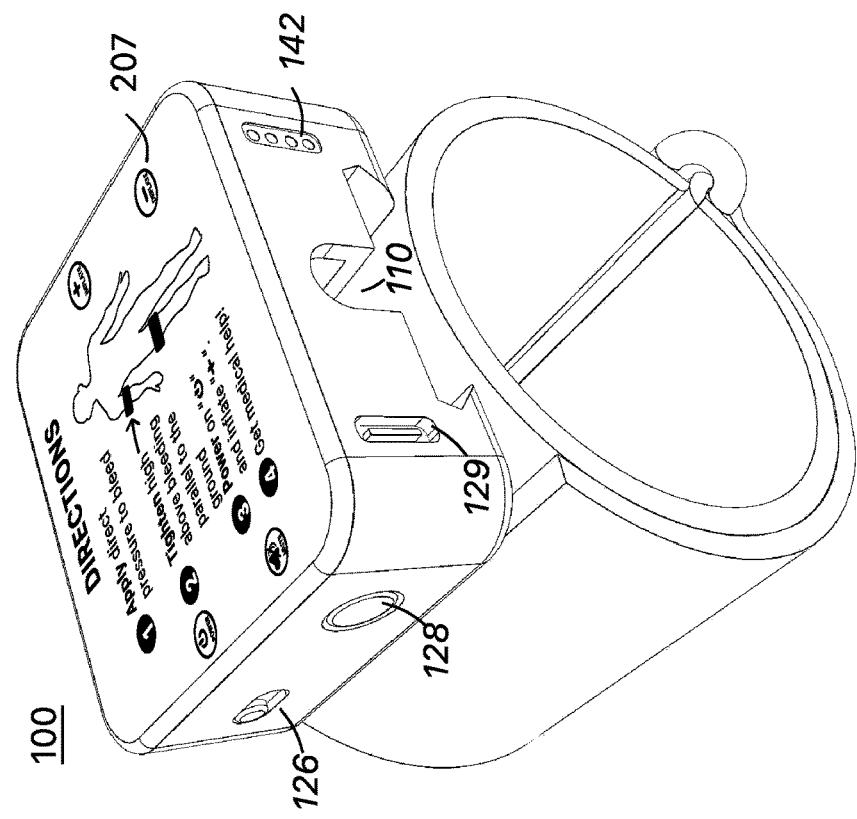
FIG. 1I shows an alternative tourniquet embodiment where the valve is located at a 90 degree angle and the shape of the controller is square.
Figure 1I:
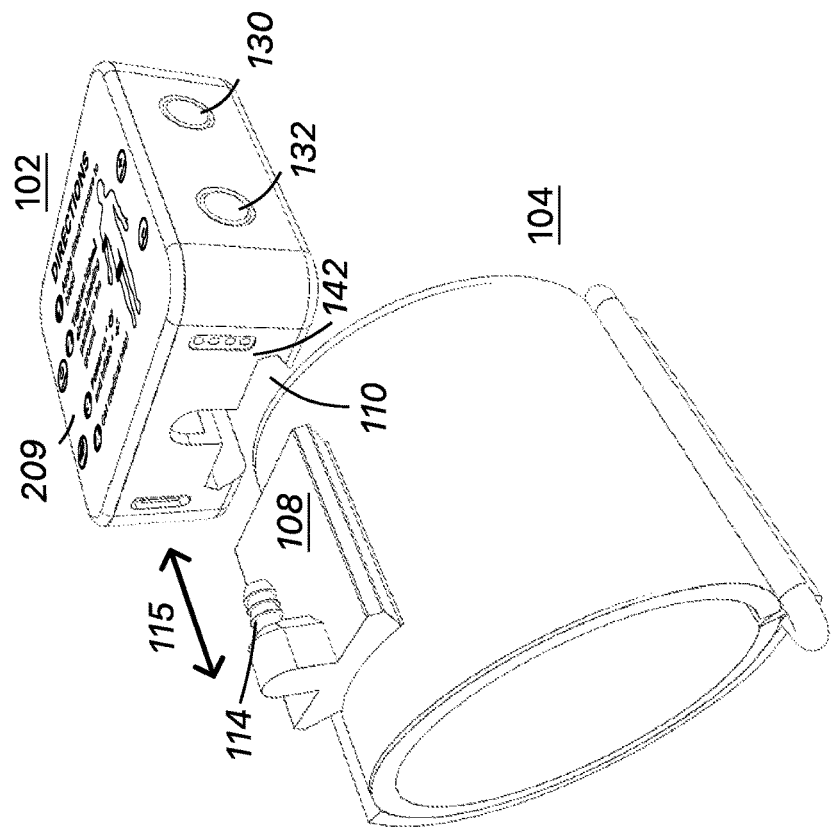

FIG. 1I demonstrates another embodiment of the tourniquet 100. Control 132 and corresponding label 207 are for deflation of the tourniquet 100, which is particularly desirable for a medical professional where tourniquets are often removed to assess bleeding and then reapplied if necessary. The placement of upper valve 114 is at a 90 degree angle in this embodiment, and the sliding mechanism 110 begins on the edge of the TQController 102 rather than in the center. The slider 108 slides directly into the side of the case in this embodiment following arrow 115. Those skilled in the art will recognize that there are a variety of placement alternatives for where the cuff 104 may enter or where upper valve 114 may be configured on cuff 104 and the end goal of fluid integration is preserved.

Additionally, the "deflate" button 132, "inflate" button 130, "mute" button 128 and "power" button 126 controls may be switched for alternative controls. In the case that the TQController 102 does not have an LCD screen 131 as in FIG. 1H, it may be desirable to include a control that would allow the TQController 102 to communicate status through a speaker, such as time applied, pressure applied, etc. This embodiment includes a speaker 142, which is optional depending on the material with which the TQController 102 is manufactured. For example, it may not be necessary to include speaker holes if the material is thin enough to hear through. When application is desired, pictorial instructions 209 are provided to facilitate rapid application and speaker 142 delivers further instruction. The instructions may alternatively be communicated through an external device such as a nearby phone, or may be limited to the pictorial instructions affixed to the top of the case. This unit may also contain a charging port 129.

Figure 1J:
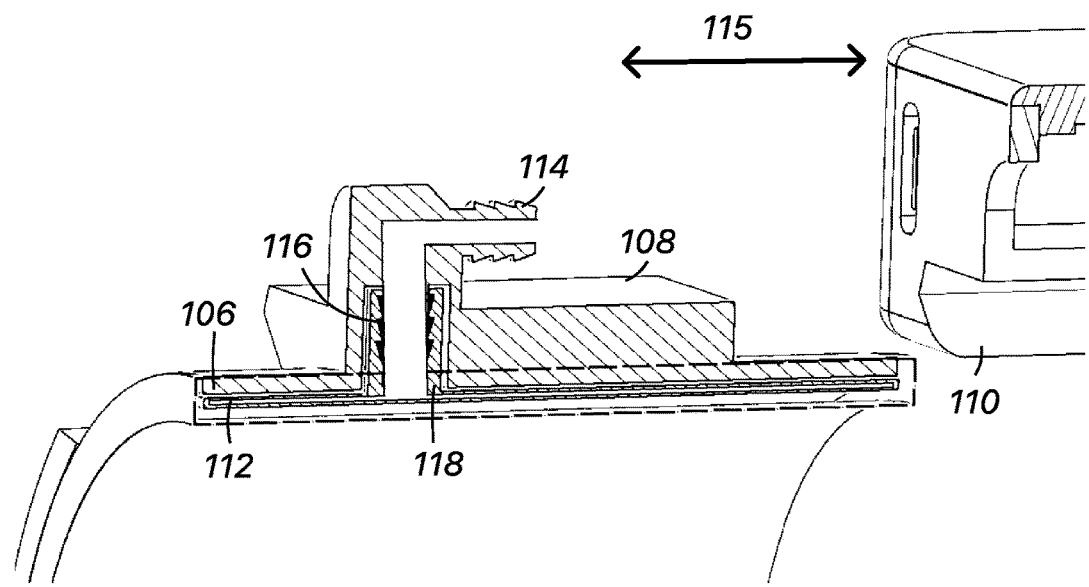
FIG. 1J shows a sectional view of attachment for the embodiment demonstrated in FIG. 1I.
Figure 1J:
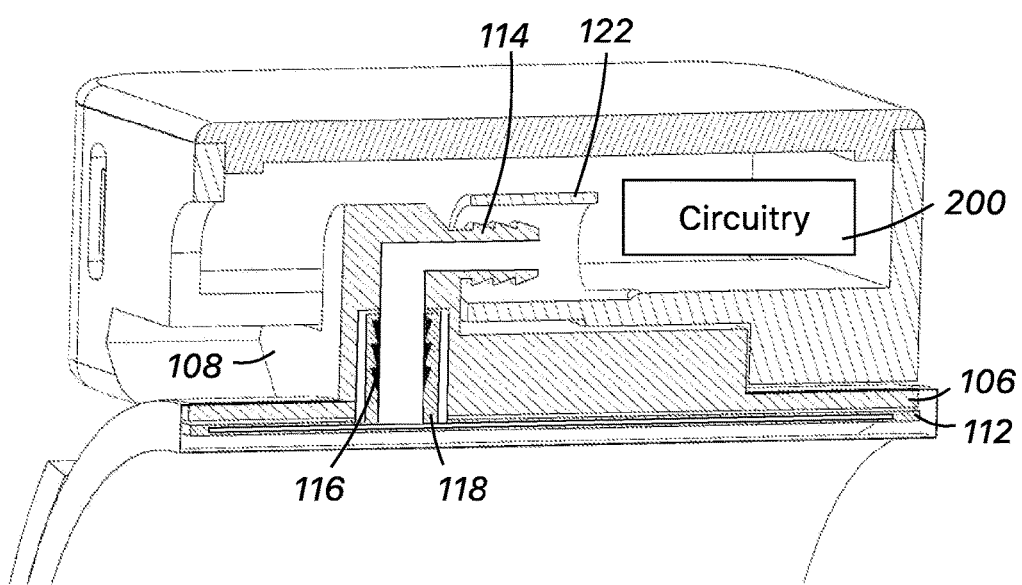

FIG. 1J demonstrates a sectional view of the tourniquet embodiment shown in FIG. 1I. The TQCuffs slider 108 integrated into the limb conforming component 106 enters into the TQController's receiver 110. The upper valve 114 enters into the tubing guide 122 along arrow 115, where the air pump 219 shown in FIGS. 2A-2B then pressurizes the inflatable member 112 under direction from the microcontroller 210 shown in FIGS. 2A-2B. To remove this connection, the units are disconnected following arrow 115. Like FIGS. 1D and 1E, the inflatable member's upper tube 118 is fastened around the limb conforming member's internal lower valve 116. The electronics 200 then controls the inflation process.

Figure 2A:
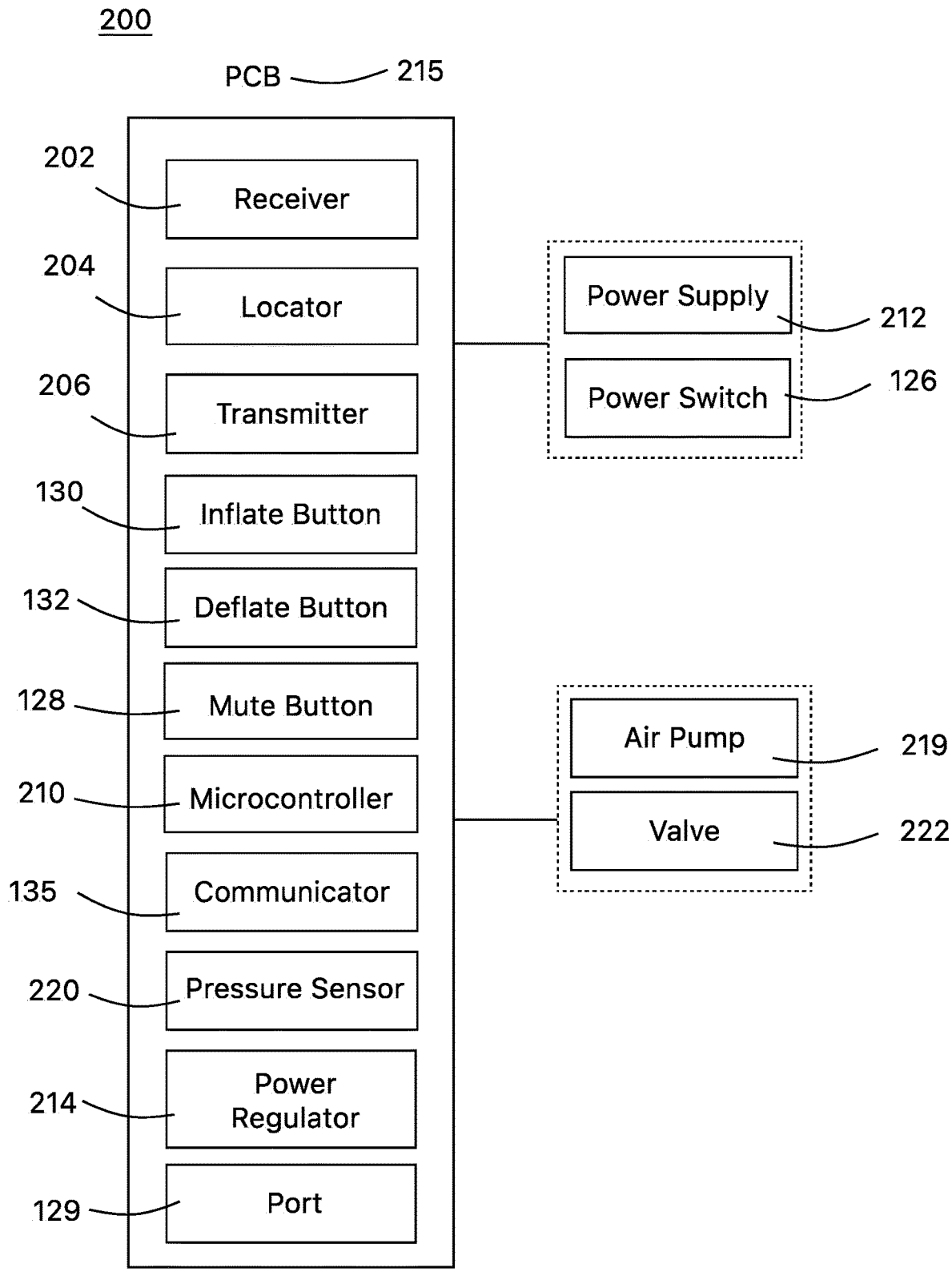
FIG. 2A shows a circuit diagram of the TQController.

FIG. 2A illustrates a block diagram showing the electronics contained inside of TQController 102. To facilitate the inflation, deflation, and pressure regulation of the cuffs inflatable member 112, the electronics 200 incorporates an air pump 219, a pressure sensor 220, and a valve 222. These components are connected to the PCB 215 and controlled by the microcontroller 210. The air pressure introduced into the inflatable member is monitored by a pressure sensor 220. In certain embodiments, valve 222 is an electronic valve designed to regulate the direction of air flow such as a solenoid. Valve 222 offers flexibility, allowing for manual adjustments or electronic control, thereby enabling precise management of air flow. The pressure sensor 220 indicates when optimal pressurization is achieved, allowing the microcontroller to navigate to the next logic point demonstrated in FIGS. 2E and 6.

The electronics 200 includes power components including a power supply 212, power regulator 214, port 129 and power switch 126. The power supply 212 may be in some embodiments a rechargeable battery such as a lithium-ion polymer (LIPO) battery compatible. Alternatively, the power supply may be a disposable battery, battery pack, or AC/DC power supply. If the tourniquet is used in conjunction with a TQ Station in FIG. 3, the battery will likely be rechargeable, and it may include a port 129 to receive power. In some embodiments the port 129 is a wireless charger. The power supply 212 is regulated by a power regulator 214 and activated by a power switch 126. In some configurations, the tourniquet 100 includes an "idle" mode, where it can be on but in a power saving state to preserve battery life, in which case activating any control would awaken the tourniquet from idle mode. Alternatively, once the tourniquet 100 is applied to a limb and the pressure sensor 220 detects a change in pressure, the tourniquet 100 may awaken automatically. The power supply 212 and regulator 214 can incorporate advanced power management features, such as energy harvesting from ambient sources or adaptive voltage regulation systems to optimize power efficiency and extend battery life. These power saving sources and ambient harvesting sources are especially beneficial in prolonged care (PC) scenarios where casualties may be displaced, or active combat theaters where medics are unable to access insecure areas.

The PCB 215 includes several components. Transmitter 206 transmits collected data from the TQController 102 to a centralized server 500, shown in FIG. 5, allowing outside access to data and explained in detail below. Various communication methods can be employed to transmit data from the tourniquet 100 to the centralized server 500, such as the microcontroller's optional Bluetooth module, as explained previously. Alternatively, the transmitter 206 can be a SIM Card, enabling connection to emergency services such as 911 through a cellular network. Alternatively, long range radio (LORA) or a similar method can be employed. Data can be aggregated into a SQL database or other acceptable data storage configuration.

Receiver 202 is configured to receive data or communication from an external source, such as data stored in the centralized server 500. This data can range from hardware and software version to the patient's ideal limb occlusion pressure (LOP).

Communicator 135 allows for the delivery of stepwise instructions. In some embodiments the tourniquet allows a 911 dispatcher to communicate with those at the scene of the emergency. This is particularly useful in the case of multiple injuries on one casualty, a mass casualty incident, or if a patient is self-applying a tourniquet 100. The communicator 135 may be a speaker 142 shown in FIG. 1I, an LCD screen 131 shown in FIG. 1H, or an LED light 125 shown in FIG. 1A. Alternatively, the communicator 135 may be an extraneous device such as a mobile phone or computer application where instructions and status are delivered separately from the tourniquet 100, or may be disabled in favor of the pictorial instructions affixed to the device 209 in FIG. 1A.

Locator 204 can use various methods to provide location data, such as cell tower triangulation, GPS data, Wi-Fi or Bluetooth positioning, or beacon-based positioning. The locator 204 may be removed depending on the microcontroller's locating capabilities. The location can be pre-set upon device configuration and thus live location is not needed. Alternatively, if cellular connection is enabled, the controller 102 can use Automatic Location Identification (ALI), which is used by Public Safety Answering Points (PASPs) to receive and display information about the caller, thus eliminating the need for a separate locator. PASPs are usually monitored by dispatchers who can promptly dispatch responders to the given location. The specific implementation and infrastructure can vary between countries and regions. For example, it may be desirable to have a more rugged GPS based locator for a military application where casualties may be in remote areas, or to eliminate the locator in a suburban or metropolitan area in favor of reliance on ALI or Wifi location. Capability exists for the tourniquet 100 to connect remotely to another GPS location device, for example, to a cell phone's Bluetooth or hotspot, a boat's EPIRB system, or an independent GPS locator's system. If used in conjunction with a TQStation in FIG. 3, location capabilities may be overridden in favor of pairing with the locator or preset location on the TQStation.

Location capability may be utilized to find casualties displaced within a building, which is particularly helpful in the case of buildings with multiple floors or rooms. This would be executed by programming the tourniquet 100 with the floor and room number it is stored in; activating the tourniquet 100; transmitting the location and status of the tourniquet 100 to the network upon activation; providing a location database for the building, wherein the location database comprises information on the floor plan and room numbers of the building; receiving the location and status information of the tourniquet 100 from the transmitter 206; transmitting the location information of the casualty to at least one remote emergency dispatcher and at least one first responder within the vicinity of the building; updating the location of the casualty in the network if the tourniquet 100 is moved; and providing instructions to the dispatcher and first responder to locate and assist the casualty based on the location information received. Advancements in technology may further change the methods used to communicate.

Advanced pressure control algorithms can be employed, ensuring precise and automated pressure adjustments based on the specific needs of the patient. This can take into account a patient's blood pressure and calculate personalized pressure, such as limb occlusion pressure (LOP). LOP is common practice for finding the minimum effective tourniquet pressure for a patient in controlled environments, such as operating theaters. Finding LOP in the field is difficult unless the patient is very still. Therefore, blood pressure values may be uploaded to the tourniquet's database during initialization to calculate the necessary pressure more accurately. The tourniquet 100 may incorporate additional sensors to detect undesired blood flow, such as a secondary pressure sensor, a small Doppler ultrasound, etc., or incorporate feedback mechanisms for monitoring and sustaining optimal pressure levels during usage. RFID tag 224 and RFID reader 225 shown in FIG. 1G may further be incorporated into the electronics 200 to facilitate rapid inflation to an ideal pressure. These may be used to store and read additional tourniquet information as aforementioned.

Further, in a scenario where casualties do not have rapid access to medical treatment, it may be desirable to initiate a partial or complete reperfusion protocol after a certain amount of time has passed to reinstitute blood flow to the limb. This can occur at preset time intervals or can be done on demand through the mobile application, and in some embodiments can be preset through a button or other feedback mechanism. More basic pressure adjustments are accomplished using the included inflate button 130 and deflate 132 button. These buttons and the mute button 128 can be removed in favor of controls on a mobile application, which may be desirable to avoid a patient accidentally activating an inflate or deflate control, thus loosening or tightening the tourniquet 100 unintentionally. The inflate and deflate features may incorporate safety mechanisms that require additional confirmation to inflate or deflate prior to executing the command.

Figure 2B:
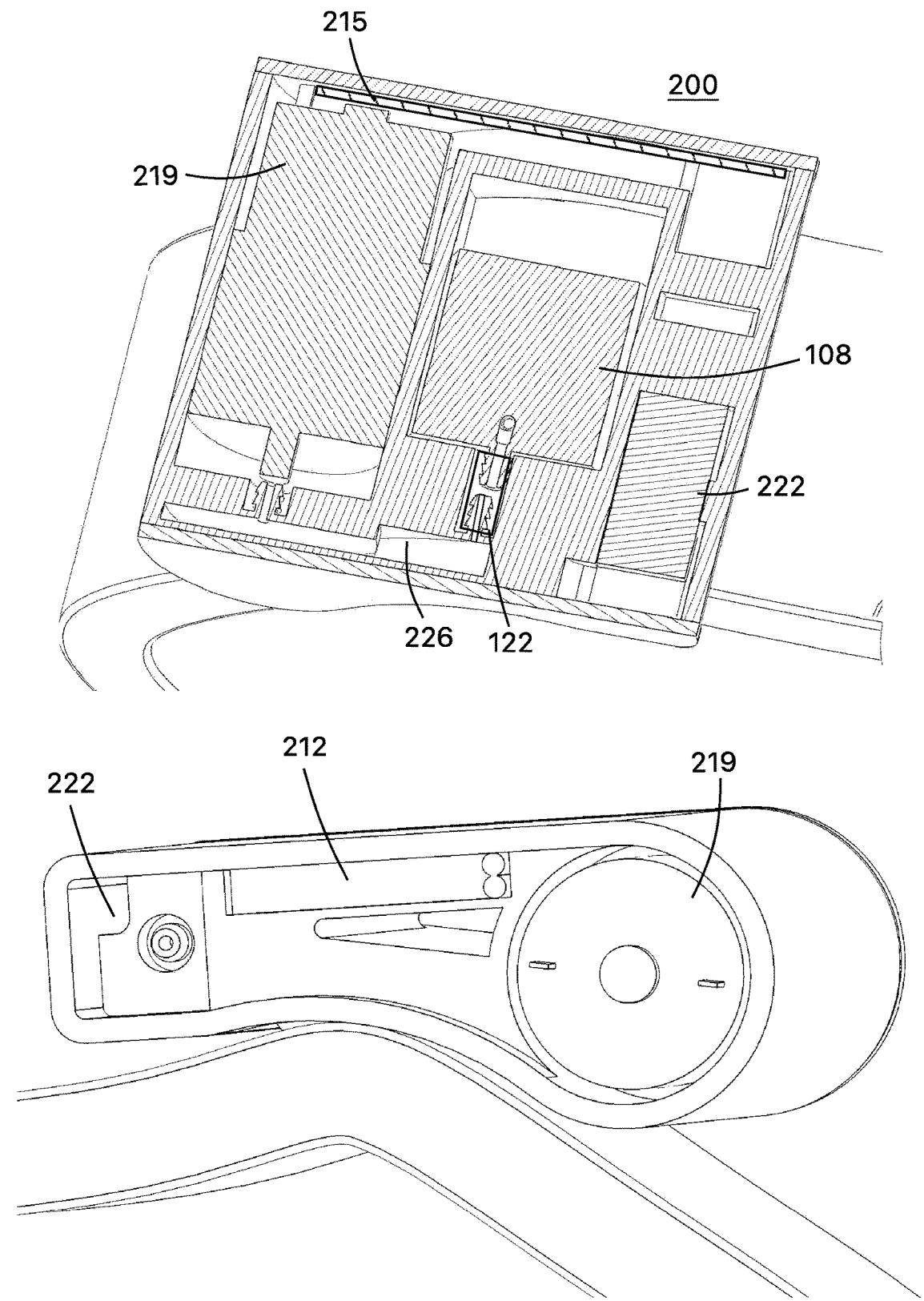
FIG. 2B shows the electronics stored in the TQController.

FIG. 2B demonstrates an exemplary TQController 102 circuitry 200 storage means. Here, an integrated air pathway 226 accomplishes rapid inflation of the cuff 104, eliminating the use of multiple independent tubes which can be complicated and time consuming to manufacture. PCB 215 is located across the side of the TQController 102, facilitating rapid connection between the air pump 219, valve 222 and battery 212. Each component is slid into the case and can either be soldered or snapped onto the board, which reduces manufacturing time significantly. Additionally, the case is manufactured to easily slide each component in, which stabilizes each component and reduces the likelihood of breakage.

Figure 2C:
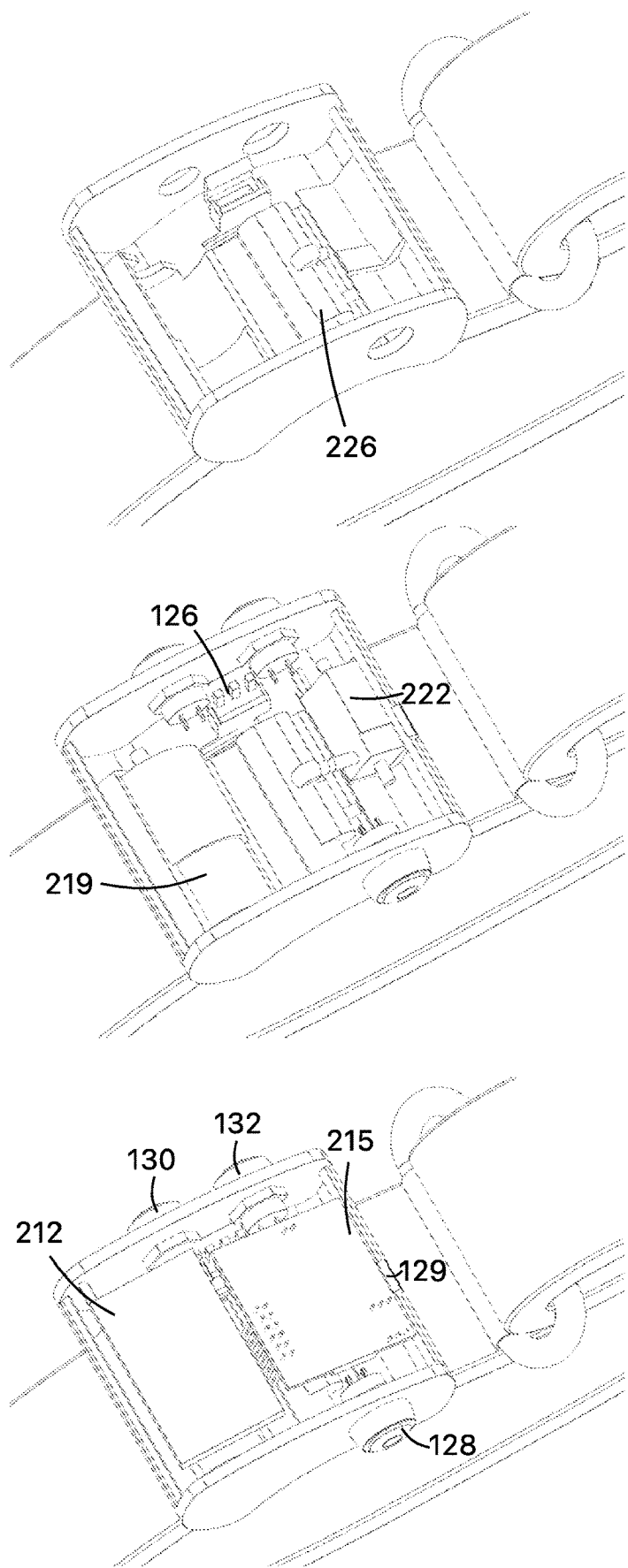
FIG. 2C shows the electronics stored in an alternative embodiment.

FIG. 2C shows an alternative storage embodiment for TQController circuitry 200, which further comprises controls 128, 130, and 132. This embodiment is curved to mold to the shape of a limb. The air pathway 226 is integrated into the bottom of the case rather than the side of the case. The power switch 126 is integrated into the bottom of the case to prevent accidental shutdown during application. The air pump 219 and valve 222 are placed across from one another and here are snap-fit into the case rather than slid into housing. The PCB 215 includes a port 129. The battery 212 is placed adjacent to the board before the case is closed.

Figure 2D:
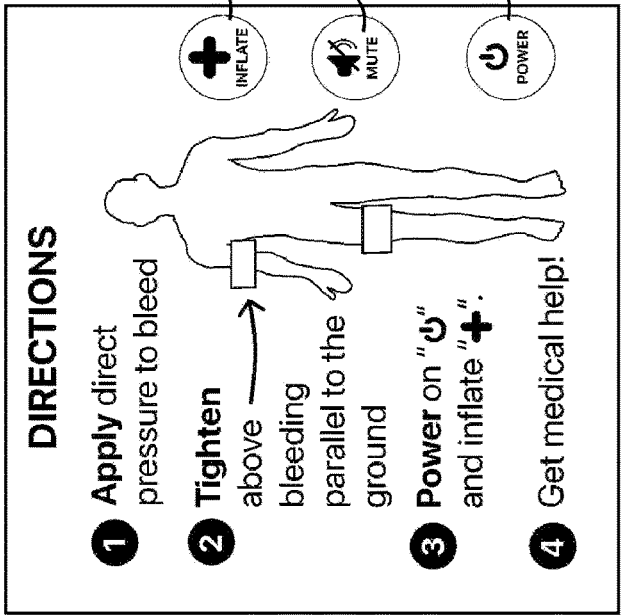
FIG. 2D shows pictorial instructions placed on top of the tourniquet in some embodiments.
Figure 2D:
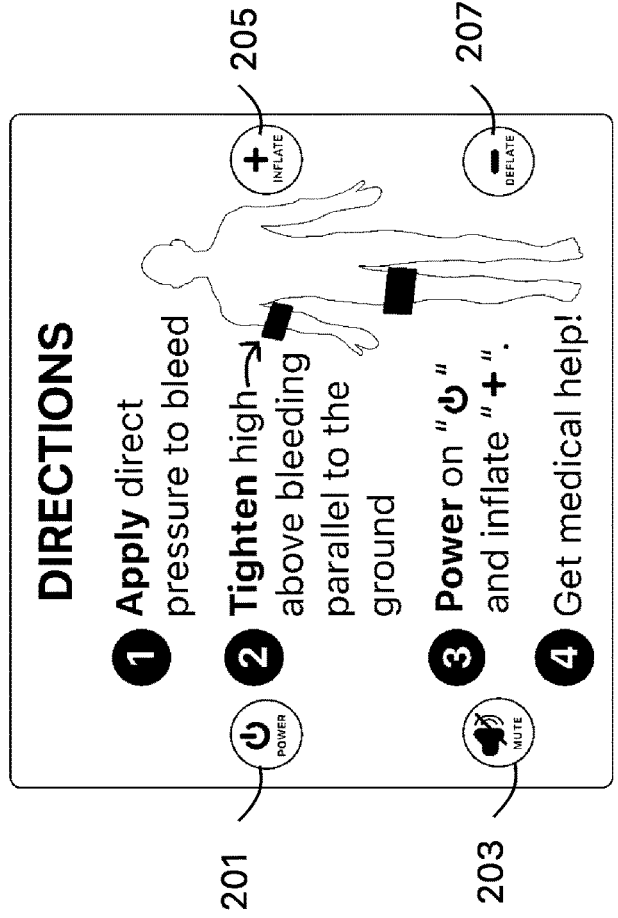

FIG. 2D shows the pictorial instructions 209 in two different embodiments; one includes control labels 201, 203, 205, and 207 dispersed around the edges of the controller, while the alternative embodiment includes fewer control labels 203, 205 and 207 on only one side of the controller. There are a number of different arrangements that could be made out of the pictorial instructions that would still preserve the functionality of the system. It may be desirable to place controls on opposite sides to prevent accidental selection of the wrong control, or to eliminate the controls altogether in favor of using controls in the mobile application shown in FIG. 4E.

Figure 2E:
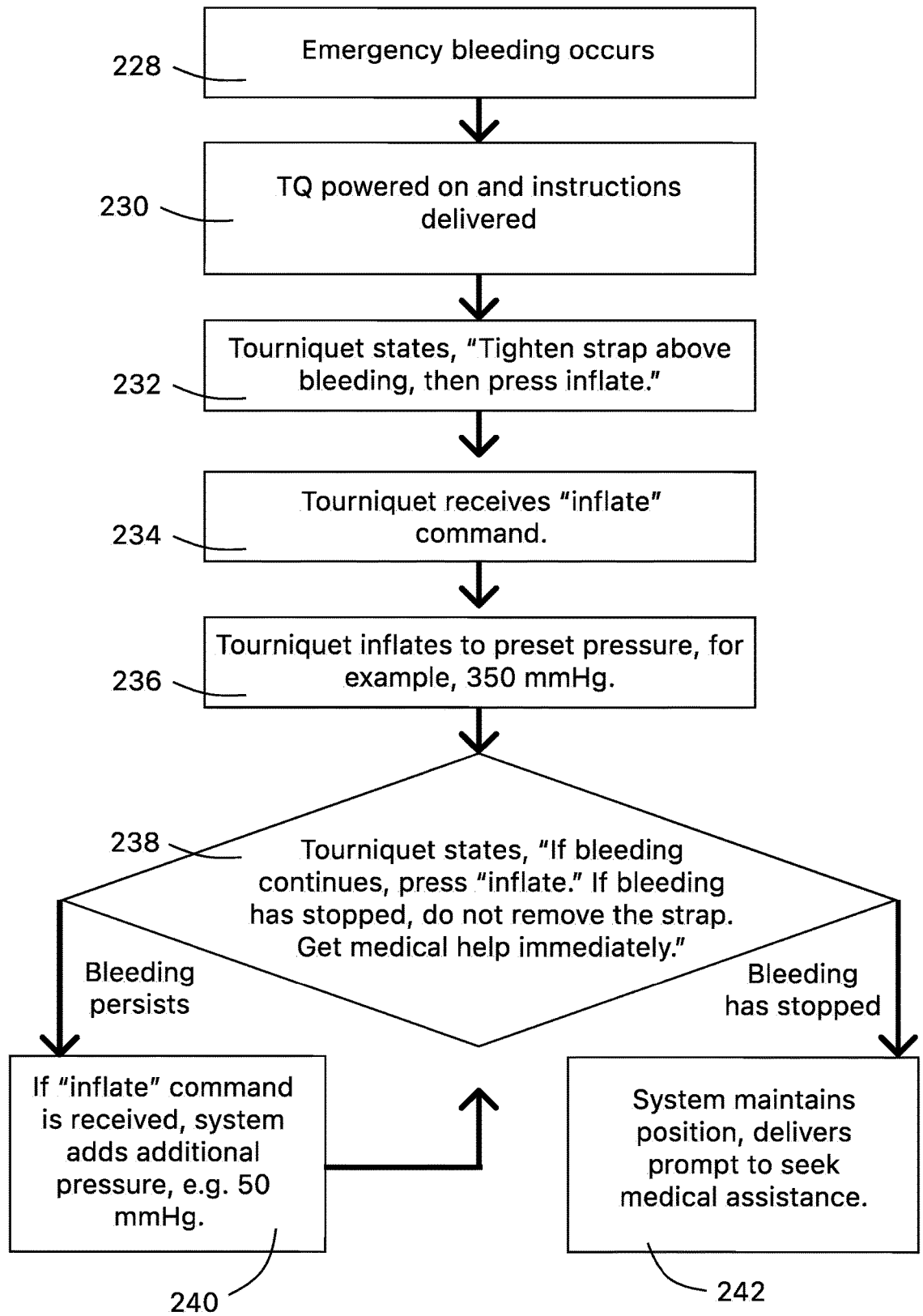
FIG. 2E shows a method in which the tourniquet is applied after bleeding is identified by a witness.

FIG. 2E demonstrates exemplary methodology of how tourniquet 100 can stop blood loss. First, an emergency bleed occurs, at step 228. The tourniquet 100 is then secured by sliding the cuff fabric 119 through the loop 117, pulling the fabric as tightly as possible, and securing the hook and loop 121 by doubling the strap back as shown in FIG. 1. The device is powered on or awakened out of idle mode at step 230. Questions are posed through the communicator 135 shown in FIG. 2A. Alternatively, the TQController 102 may be configured to identify when the tourniquet 100 has been applied since the pressure sensor will detect the increase in pressure from manual tightening, and it may automatically awaken out of idle mode. This is desirable in cases where the tourniquet 100 is likely to be used, such as in an active combat scenario, or in cases where rapid application is necessary and delay to access the tourniquet 100 is likely, such as when tourniquet 100 is stored within a TQStation in FIG. 3.

Once the tourniquet is powered on, the communicator instructs the user to "tighten strap above bleeding, then press inflate," or words to that effect, at step 232. When the "inflate" command is received at step 234, the tourniquet tightens to a preset pressure, at step 236. The preset pressure may be obtained through varying methods, such as a database of pressures corresponding to different cuffs, customized pressure, or an RFID tag associated with the particular cuff. The tourniquet states, at step 238, "If bleeding continues, press "inflate". If bleeding has stopped, do not remove the strap. Get medical help immediately," or words to that effect. If bleeding has not ceased, the "inflate" command is received again at step 240, the tourniquet adds pressure, and reposes the question 238. If bleeding has ceased, the device delivers a prompt to seek medical help, at step 242.

In some embodiments, instructions may be triggered by sensors that verify proper use of the tourniquet. For instance, if the device is powered on before being properly positioned above the bleeding site, the device may verify correct placement before initiating the tightening process by detecting a base pressure as aforementioned. The controls may also be moved and perform similar functions. For example, the deflate control may be hidden or may be removed in favor of control from an external device to prevent accidental deflation of the tourniquet. The pictorial instructions 209 in FIG. 2D are complemented by instructions conveyed through the communicator 135. In certain embodiments, the pictorial instructions 209 can be substituted with a touch screen or a screen 131 such as in FIG. 1H, enabling the display of interactive instructions. Those skilled in the art will recognize that there are multiple suitable methods for delivering instructions or formatting them.

Figure 3A:
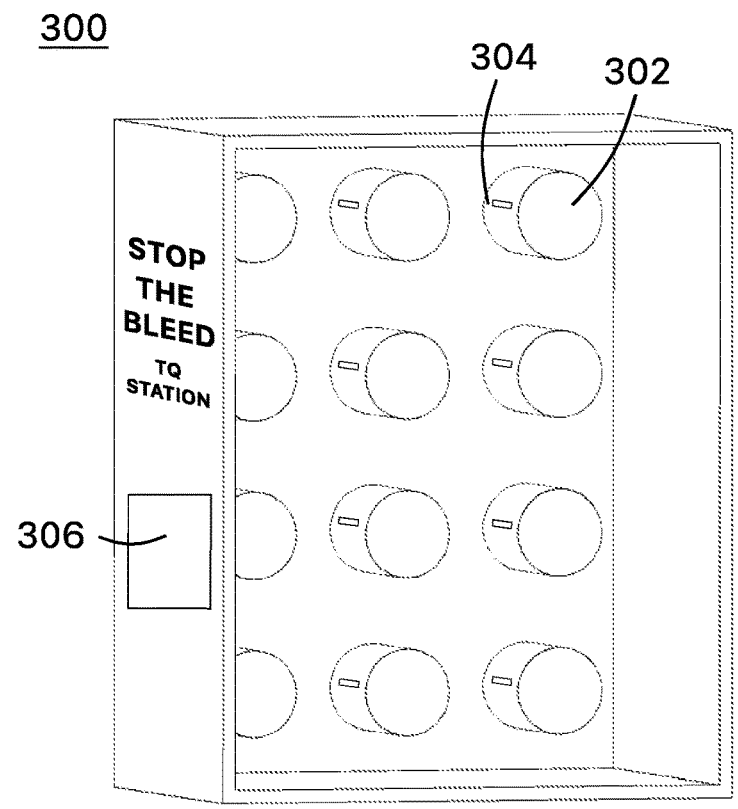
FIG. 3A shows a tourniquet station where full tourniquets are stored.
Figure 3A:
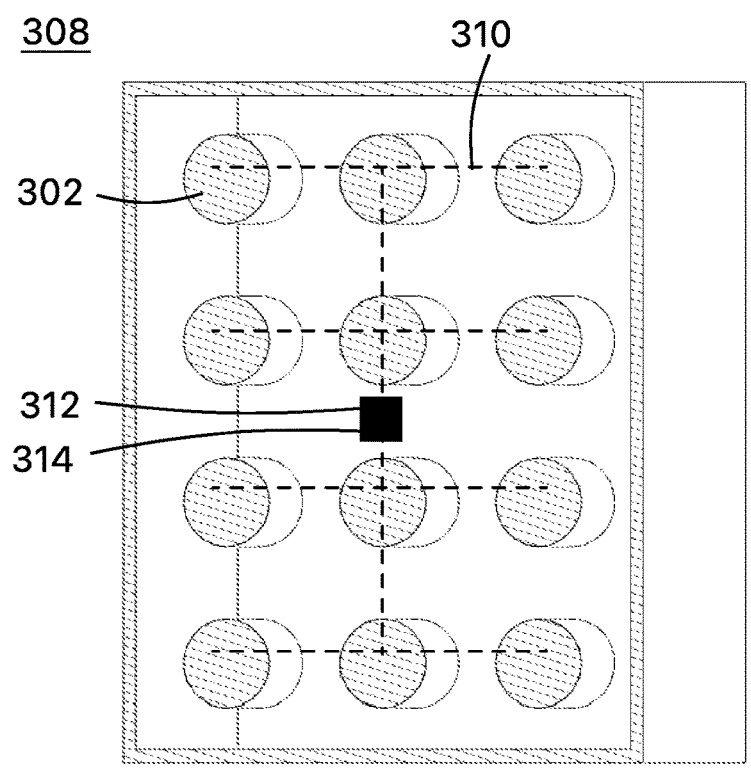

FIG. 3A shows a TQStation 300 in front view and in a back view 308, where a plurality of tourniquets 100 may be contained. The TQStation 300 contains docks 302 and charging mechanisms 304. Twelve docks 302 are shown in FIG. 3A, however this is not intended to be limiting as the stations can be built with a varying number of docks 302. In this non-limiting example, the docks 302 are circular, where the tourniquets 100 can be stored in a pre-looped configuration such as in FIG. 1G or 1I. They can then be secured around the docks 302 and easily pulled off when use is desired. A monitor 306 communicates data, shown in more detail below.

The charging mechanisms 304 here are wireless chargers, but can alternatively be a USB port or other connector. The back of the TQStation 308 includes interconnected charging circuitry 310 that routes each station 308 to a central charging outlet 312 regulated by the station controller 314. The central charge may be from a wall mount AC or DC power supply, or a remote or a portable power source.

Figure 3B:
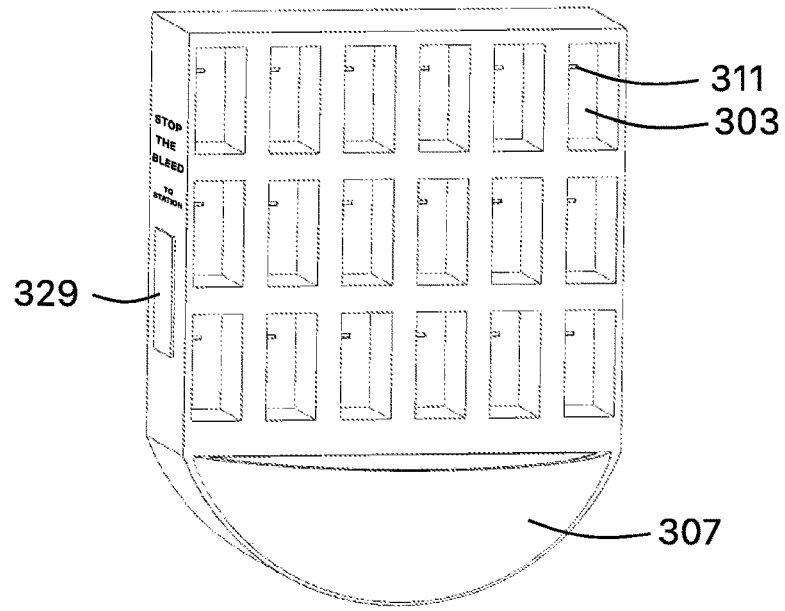
FIG. 3B shows a TQStation where TQCuffs and TQControllers are stored separately.
Figure 3B:
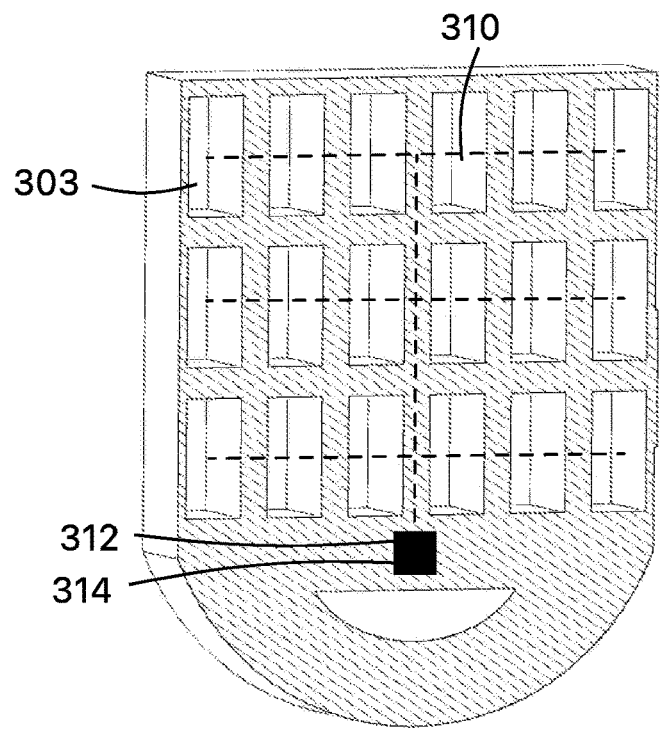

FIG. 3B shows an alternative front view 301 and back view 309 embodiment of the TQStation 300. The configuration of the docks 302 can be in a number of shapes, such as squares, slots, or holes. FIG. 3B demonstrates that the TQStation 300 can be fit solely for controllers 303 and have storage 307 for cuffs of varying sizes. Additionally, an alternative charging mechanism 311 where the tourniquet 100 is plugged in via USB to charge is demonstrated in FIG. 3B. This unit contains equivalent back circuitry 310, outlet 312 and controller 314. However, the communicator 329 is no longer a screen in this embodiment but is replaced with a speaker.

Here, two embodiments of the TQStation 300 have been shown, however these may be adjusted to fit a number of applications. It may be useful to exchange some components in favor of fully remote components that allow for use off the grid. Power units may be replaced with solar charging units in the case of a wilderness application. For a vehicular application, it may be useful to reconfigure the TQStation 300 to fit in a car trunk, or in an ambulance or other emergency response vehicle for rapid use in an emergency situation.

Figure 3C:
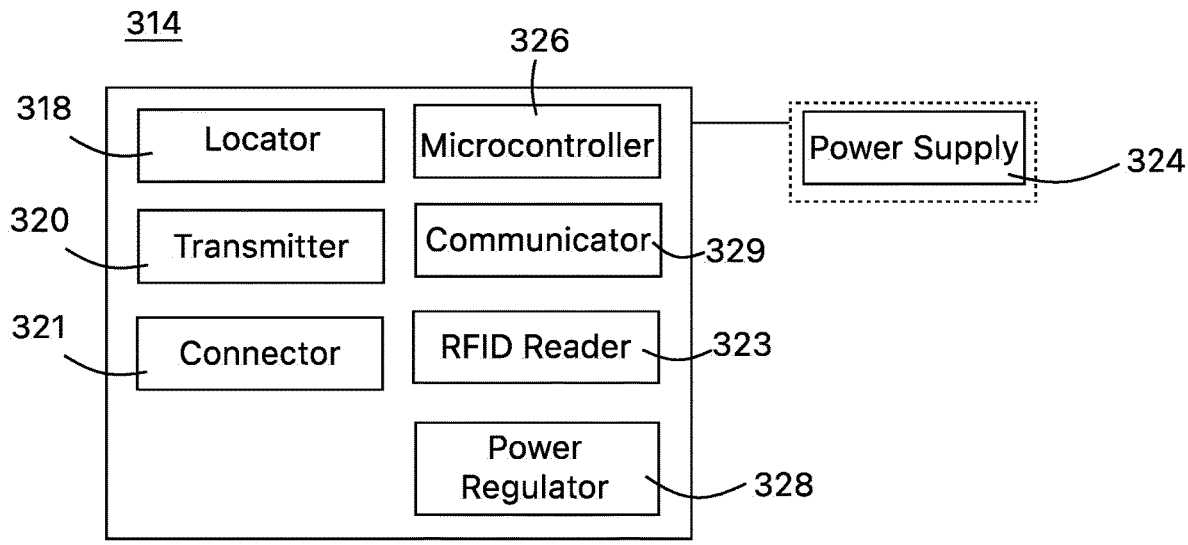
FIG. 3C shows exemplary TQStation circuitry.

FIG. 3C is a block diagram showing the components of the station controller 314 in detail. The controller 314 aggregates data received from the tourniquets 100 stored in the TQStation 300. The controller 314 is managed by a microcontroller 326. Tourniquet data can be received by firstly connecting to the connector 321, which is in some embodiments an embedded hotspot. Secondly, data is processed by the microcontroller 326 after connection is established. In the event that a tourniquet 100 is loaded onto the dock 304 without prior initialization or setup, it is optional to synchronize data with the TQ Station 300. For instance, if a tourniquet 100 is placed within a TQ Station 300 positioned near an entry point in a stadium, the communicator 329 may ask whether the tourniquet 100 should be permanently associated with this location. This communication can be accomplished audibly through a speaker, LED light arrangement, or a monitor 306 in FIGS. 3A and 3D. If confirmed, the fixed location data within the tourniquet 100 will be updated to align with the station's data. Stations 300 have the capability to override previously stored location data when tourniquet 100 is transferred from one station 300 to another.

Figure 5:
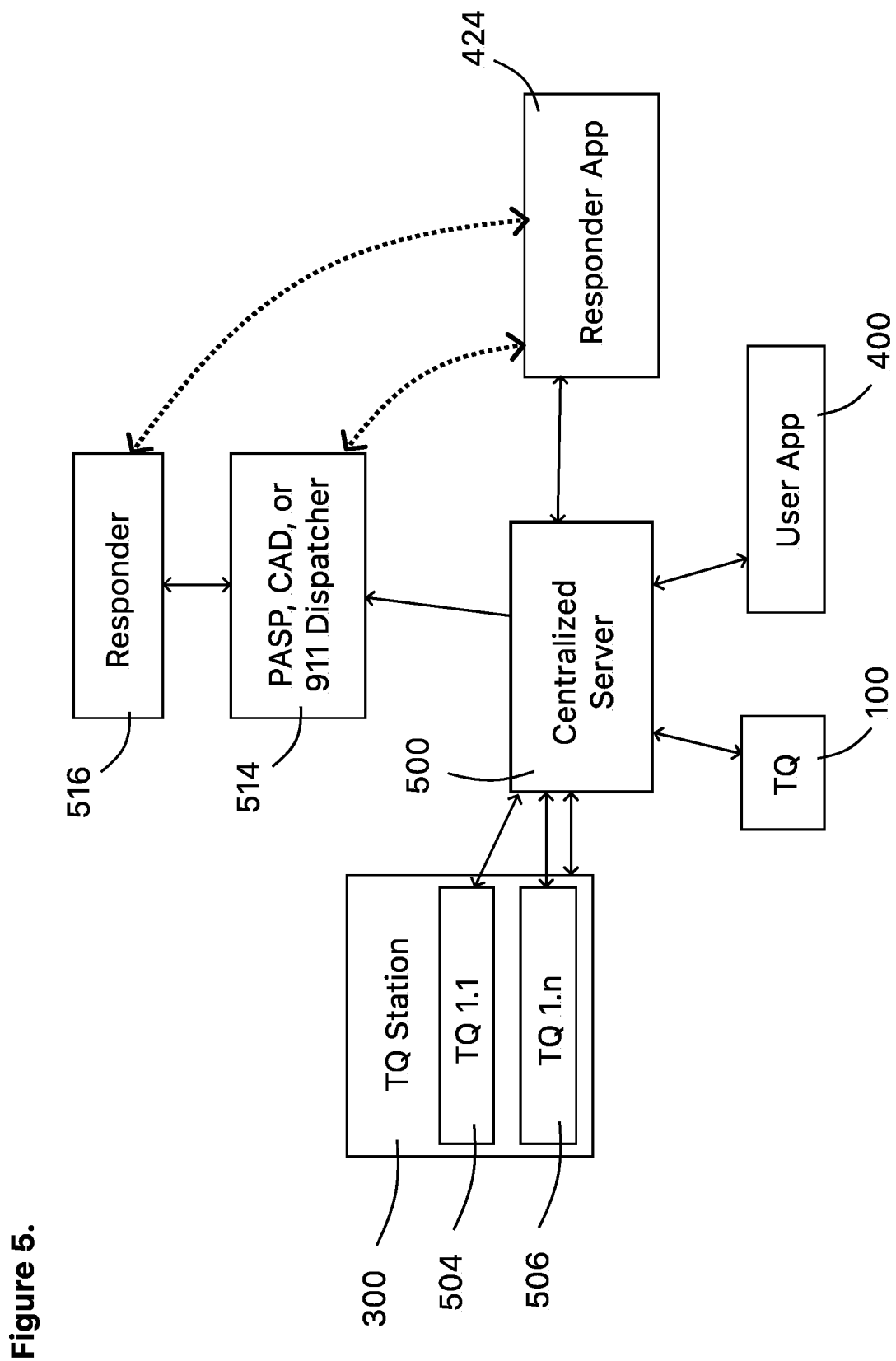
FIG. 5 shows the TQNetwork.

A transmitter 320 communicates data about the tourniquets 100, including the aforementioned fixed and variable metrics, to the centralized server 500 in FIG. 5. Data can then be aggregated into a SQL database or other acceptable data storage configuration.

A locator 318 reports the location of the tourniquet station 300 to the centralized server 500. The connector 321, microcontroller 326, locator 318, and transmitter 320 can use any of the methods previously described to obtain and report location data and communicate it with the centralized server 500 in FIG. 5.

The controller 314 is connected to a power supply 324 that can be provided via outlet 312 in FIGS. 3A-3B. A power regulator 328 may be included. Each tourniquet 100 may be in the TQStation 300 in either "off" mode, "on" mode, or "idle" mode. In some embodiments, the front of each tourniquet's charger 304 or 311 or dock 302 or 303 may contain an RFID tag that allows an external device to receive and display status, and troubleshoot connectivity issues through the site. Here an RFID reader 323 can be wired to each port or to one location. Alternatively, a motion sensor or mechanical switch may be present to detect a tourniquet.

Once a tourniquet 100 is employed in an emergency, the station's controller 314 sends an alert to the centralized server 500 that the tourniquet 100 is in use, and this can simultaneously be reported to each connected device with access to the TQStation 300 via a text message, phone call, or other acceptable alert. The TQ Station controller 314 may automatically update how many tourniquets 100 are available for use to the centralized server 500 based on how many tourniquets 100 are present within the station 300.

Figure 3D:
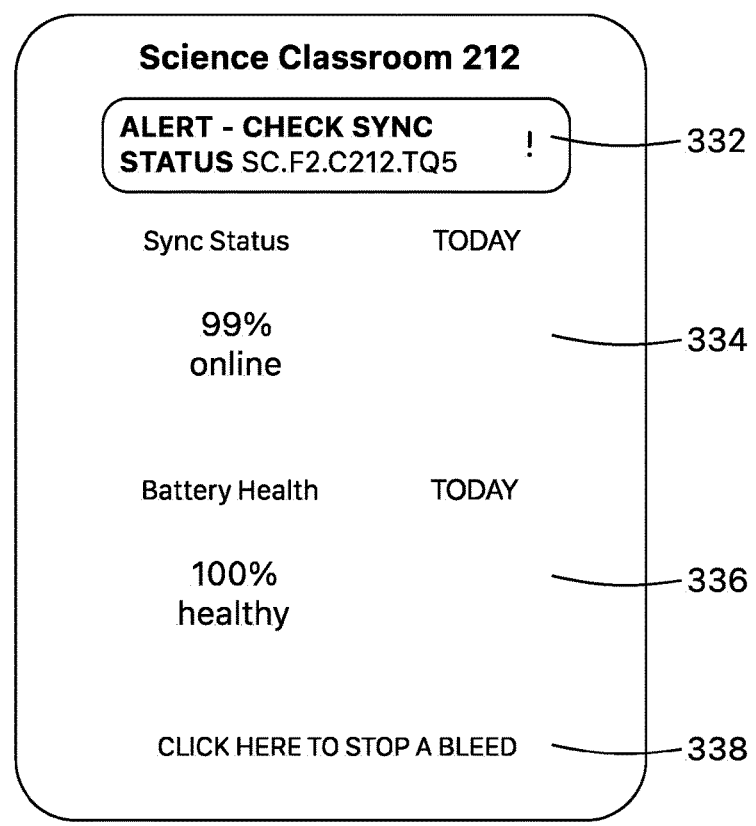
FIG. 3D shows an exemplary TQStation display.

FIG. 3D shows the monitor 306 in more detail. Here the monitor 306 displays the sync status 334 and battery health 336 of the tourniquets contained in the station 300. In this example, one tourniquet 100 has failed to sync, and thus an alert 332 is displayed indicating a problem with sync status. The labeling convention of alert 332 follows a standard convention labeling the type of building, floor, classroom, and tourniquet number, but since this system can be used in a variety of settings and building types the labeling can be adjusted to reflect each. Alerts can be shown for a variety of device checks and failures. Here, the primary indicators of health are sync status and battery, however indicators may be programmed to show any number of notifications such as expiration dates of components, last use, updates needed, etc. If a bleed is identified, the "click here to stop a bleed" button 338 can be engaged to activate the centralized server and request emergency medical response (see FIG. 6).

Figure 4A:
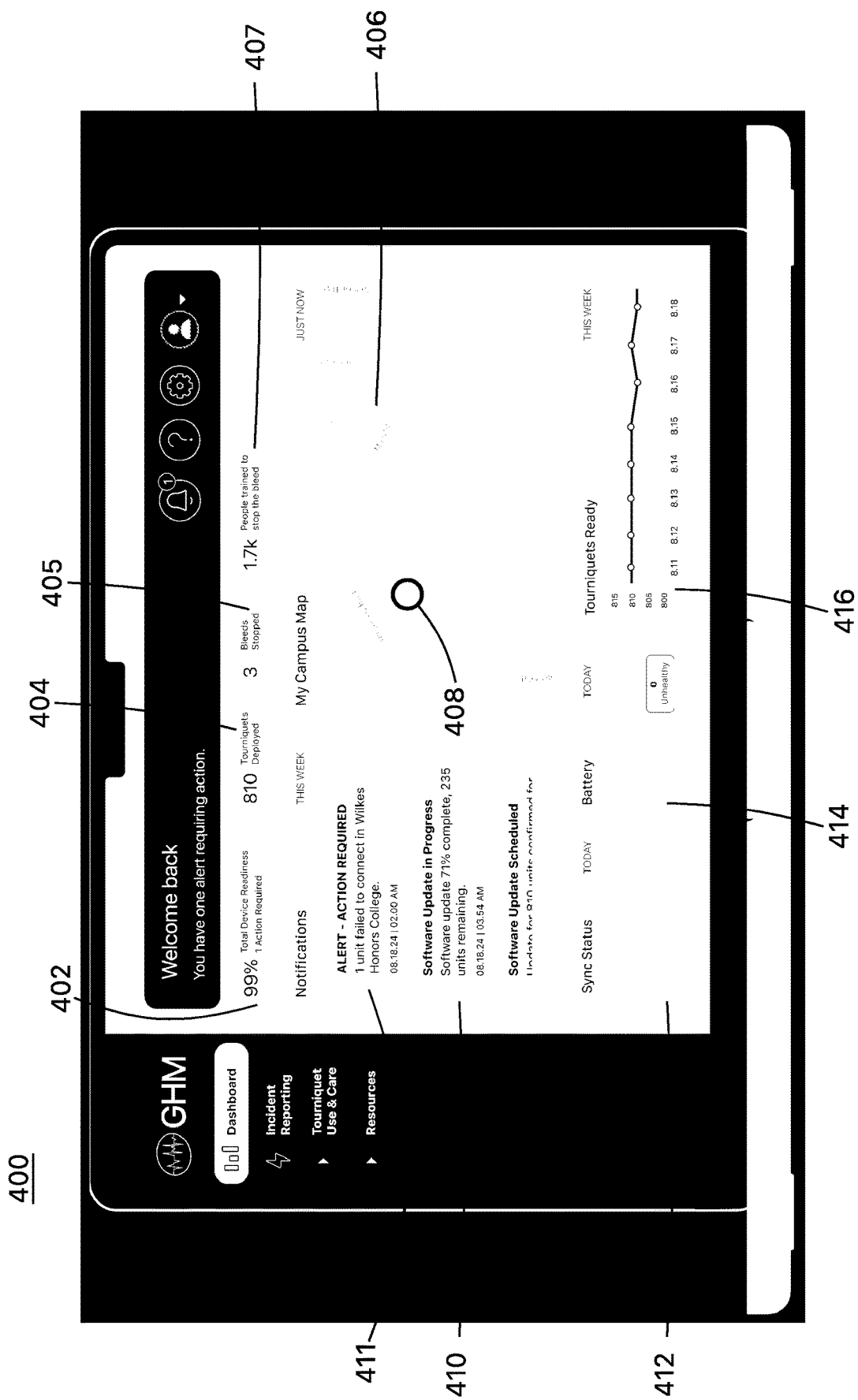
FIG. 4A shows a user application.

FIG. 4A demonstrates a tourniquet 100 monitoring embodiment through the User App 400, which shows the location and health of the tourniquets 100. FIG. 4A is a non-limiting example of a home view of the User App 400 for a school. This can be reformatted to adjust for the type of organization, for example, an office, gym, stadium, airport, etc.

A summary of tourniquet statistics is depicted across the top, showing total device readiness 402, the number of tourniquets deployed 404, the number of bleeds stopped 405, and the number of users trained to stop the bleed 407. These can be reordered to suit the organization's individual needs.

Alerts 410 include software updates, tourniquet use history, expired components, and other indicators. In this example, the most recent notification shows that a unit failed to connect 411. This is further reflected in Sync Status 412, indicating that one unit failed to sync.

Battery levels 414 are shown for the tourniquets 100, and a graph of tourniquet readiness 416 indicates the total device readiness over time. Map 406 includes all of the major tourniquet stations 300 aggregated to a building level. Circle 408 shows the building where the tourniquet 100 failed to connect. This may be a different color than the "ready" units, and here is outlined in black.

Figure 4B:
FIG. 4B shows another screen of a user application.

FIG. 4B demonstrates what occurs once the highlighted circle 408 or the alert notification 411 in FIG. 4A is selected. The site navigates to screen 418, showing a detailed view of the building where the disconnected tourniquet 100 is located. Summary box 420 shows the classroom, floor number, and failed tourniquet unit number, and can optionally show other information, such as the nearest emergency exits, or emergency assembly points. In this embodiment, data is overlaid on map 421. Alternatively, the site can display a floor plan with the tourniquet's location highlighted or other architectural modeling that for easy navigation through a building. Advantageously, this reduces the need for reliance on an external mapping platform, however if more precise navigation is necessary, "Take Me There!" 422 may open an external map platform.

Those skilled in the art may recognize that there are a number of configurations that will communicate the same essential information about a tourniquet population, and the present embodiment disclosed is not meant to be limiting.

Figure 4C:
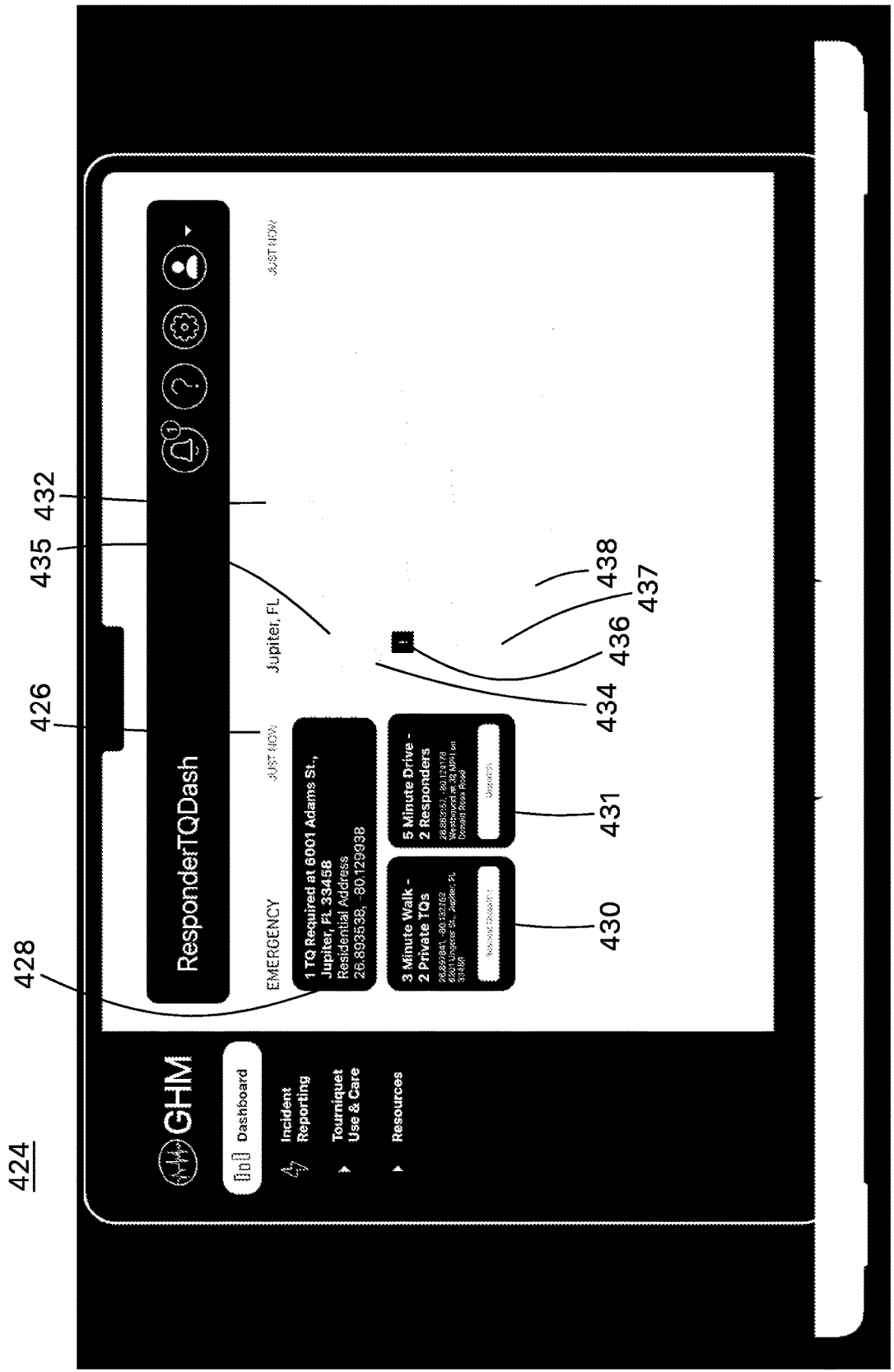
FIG. 4C shows a Responder application.

FIG. 4C shows the Responder App 424 in detail. The primary difference between the User App 400 and the Responder App 424 is that the Responder App 424 has permissions to view many tourniquets 100 in an area. The Responder App 424 is further configured to quickly facilitate the dispatch of a tourniquet 100, as time is of the essence to stop blood loss. In the event of a hemorrhage, the "Emergency" section 426 describes an emergency 428 where one tourniquet 100 is required. The "Emergency" section displays the address and coordinates of the emergency.

In one embodiment, the system encompasses optimal tourniquet selections, specifically designated as 430 and 431, which afford the operator with the premier means for deployment in an emergent situation 436. Whilst the proximity and transit time to the emergency are of importance, there are a multitude of parameters pivotal in the decision-making process for tourniquet deployment.

A consideration includes the energy reservoir level of the tourniquet 100; if found deficient, the tourniquet 100 may be deemed unsuitable for deployment. Further, the tourniquet's embedded software version holds significance; an outmoded firmware may result in the system algorithm prioritizing an alternative tourniquet 100 with a more recent software iteration.

The primary intent of the tourniquet 100 is the swift application upon a patient's extremity, ensuring cessation of hemorrhagic flow and maintaining sufficient constriction (adequate to inhibit both arterial and venous circulation) pending medical interference. Under circumstances wherein a proximate tourniquet 100 presents with diminished energy levels, and alternatives with optimal energy reservoirs are further from the incident, it might still be deemed advantageous to engage the closer tourniquet, even if its energy suffices solely for initial constriction. Alternatively, if a manual bulb is known to be connected to the electronics unit, it may be deployed over a low battery tourniquet with just the electronic inflator.

Similarly, if the tourniquet 100 has undergone recent interactions, such as cuff replacements or pressurization assessments, the algorithm might dispatch such a tourniquet over others. Certain situations might necessitate the dispatch of multiple tourniquets 100, taking into account the potential unavailability of certain responders or the varying transit times to the incident.

Illustratively, map 432 demonstrates potential tourniquets 100 for deployment. This high volume of tourniquets 100 may be common in urban areas. Tourniquets 100 in transit 437 and 438 are contained in an arrow symbol, while stationary units 434 or 435 are circumscribed within a circle. The investigative radius exhibited is relatively condensed, in alignment with the emergency's severity. In contrast, in less densely populated terrains, it might be advantageous to augment the search perimeter until a deployable tourniquet 100 is discerned.

As in this example, if a tourniquet 100 is on private property, such as in a home or office building, the Responder App 424 shows that it is a "Private TQ" 430. Further, if it is owned by a Responder or volunteer responder, who register their willingness to serve as a Responder, volunteer responder, or both, for example both on and off duty, during initial device configuration, it is indicated by the title "Responder" 431. If the user does not elect to be a Responder or volunteer responder, the tourniquet 100 will not appear on the map as an option to dispatch. If a public access tourniquet 100 is stored in an office building or gymnasium, the Responder App 424 would similarly show that the tourniquet 100 is a "Public TQ", which is similarly registered during initial configuration.

Tourniquets 100 can be dispatched by selecting "Request Dispatch" in the case of a privately held TQ 430, or "Dispatch" in the case of a responder held TQ 431.

Figure 4D:
FIG. 4D shows a phone notification requesting tourniquet dispatch.

Once the request is submitted to the centralized server 500, a notification 442 is sent which requests assistance, such as that in FIG. 4D. A number of notifications can be delivered, for example by a cell phone 440 alert notification 442 shown in FIG. 4D.

Figure 4E:
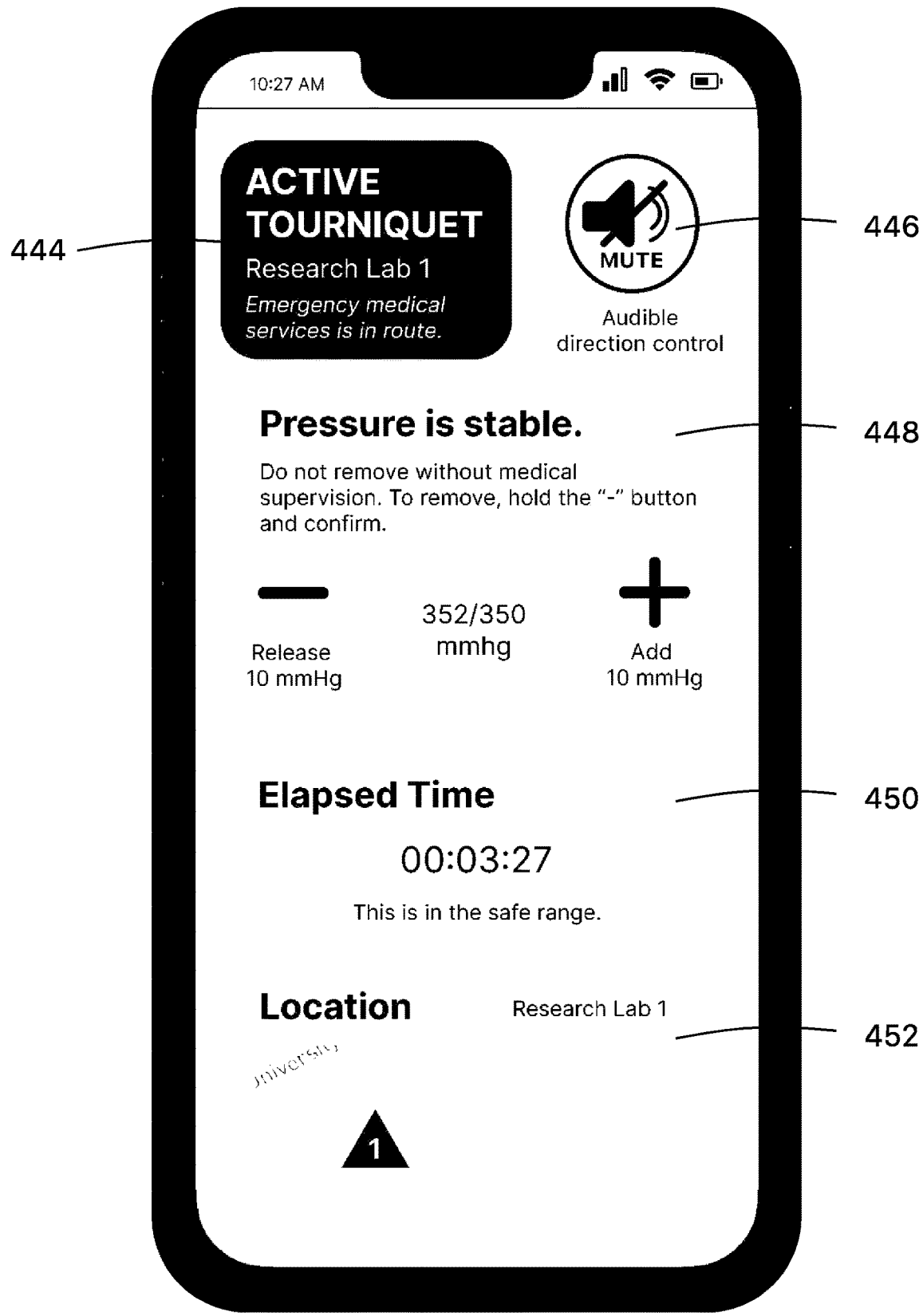
FIG. 4E shows a phone application.

The mobile application in FIG. 4E displays an option for controlling the tourniquet 100. Prior to tourniquet application, the application displays the same content shown in FIGS. 4A-4D depending on if the user is a standard user or a responder. During application, a notification is delivered that the tourniquet is active 444. As aforementioned, the controls can be used on the mobile application in addition to the buttons on TQController 102, such as the mute button 446. The app displays pressure and allows for pressure adjustments 448, shows time applied 450, and location 452. Pressure can be adjusted using the inflate and deflate feature. If a certain elapsed time period has passed, the app will present the option to slightly loosen and tighten the limb to provide reperfusion. The mobile application receives data from the centralized server 500 or directly from the tourniquet if connected via Bluetooth.

FIG. 5 shows the interaction between the centralized server 500 and a number of external systems, software, and stakeholders. The centralized server 500 receives and returns data and information from each connected section. Each section is a representation of many different potential connected devices, and the display of one of each section is not meant to be limiting since a broad number of potential connections can be made.

TQ Station 300 represents a TQ Station as shown in FIG. 3. The station 300 collects information from each internal tourniquet (TQ 1.1) 504 and (TQ 1.n) 506, as each tourniquet is connected to connector 321 in FIG. 3C. Individual tourniquets outside of a station 100 can self-report to the centralized server 500. Individual tourniquets 100 must be connected to a supporting device, for example a cell phone via Bluetooth, in order for each tourniquet's transmitter 206 in FIG. 2A to report data to the centralized server 500. As aforementioned, the TQ Controller 102 possesses the ability to provide detailed information about the tourniquet. This includes current whereabouts from GPS coordinates, a street address, building floor level, or room number/name. This data can be updated live from the locator module 204 or preset in FIG. 2A. Additionally, the controller 102 stores and reports data, such as serial number, most recent cuff replacement, etc. Moreover, controller 102 maintains records of paired devices within the tourniquet network and indicates whether the device has recently been checked or interacted with by the owner. Lastly, it utilizes a comprehensive total device readiness field, which takes into account all the aforementioned factors to determine whether the device is prepared for immediate use or not.

The data aggregated in the centralized server 500 can be reported to various stakeholders through the User App 400 or Responder App 424. In the case of an active emergency, the data may be reported to a PASP, Computer-Aided Dispatch (CAD), or 911 Dispatcher 514 and various connected responders 516.

CAD software is commonly used by dispatchers to manage police cars, ambulances, and other emergency response vehicles. TQ data can be uploaded from the centralized server 500 to CAD software 514. Alternatively, volunteer or professional responders can be deployed through the Responder App 424. Once the dispatcher assigns units to the emergency location, the dispatcher can track them via the CAD system. The responders 516 gather the necessary tourniquets 100 for the rescue, navigate to the emergency, and use the tourniquet 100 to stop the bleeding. The patient is then transported to the hospital for further treatment.

Extremity hemorrhage can cause death in very little time; therefore it is desirable to dispatch the closest available tourniquet 100 to the scene of the emergency. The applications described herein allow for rapid dispatch of the closest available tourniquet 100 to reduce mortality. The centralized server 500 can use an algorithm or algorithms of varying complexity levels to determine if the tourniquet 100 is able to be deployed or not deployed based on different combinations of factors aforementioned, such as battery health, sync status, last interaction, total device readiness, etc. The selection and dispatch of tourniquets 100 can involve a wide range of protocols, processes, and algorithms, which can vary significantly.

Figure 6:
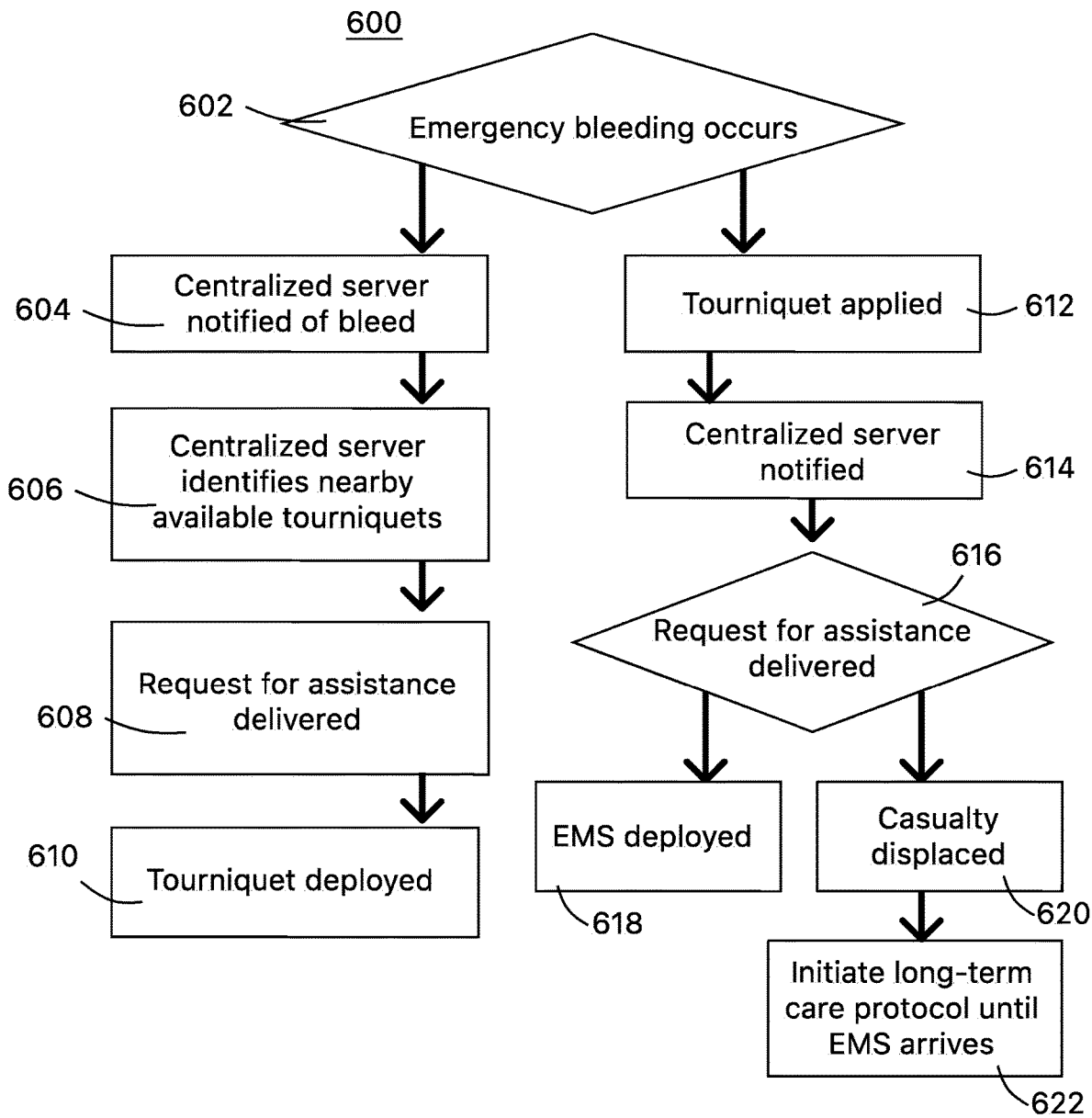
FIG. 6 shows multiple methods in which emergency bleeding is stopped with the tourniquet.

FIG. 6 demonstrates a few examples of how the tourniquet network can be activated for the purpose of deploying assistance to an emergency bleed. Network activation can begin after emergency bleeding occurs 602. The centralized server 500 in FIG. 5 is either notified of a bleed 604, which can occur for example through a call to EMS, or through the server receiving a request to stop a bleed through control 338 in FIG. 3D which may also be integrated into either of the applications shown in FIGS. 4A-4C. The centralized server then identifies nearby available tourniquets 606 shown in FIG. 4C and delivers a request for assistance 608. This request can be delivered through the onboard communicator 142 of the tourniquet in FIG. 2A, through a notification from the TQ Station Monitor 306 and or communicator 329 in FIG. 3C, through a phone notification in FIG. 4D, through PASP or CAD software, or a 911 Dispatcher 514 in FIG. 5.

During initial device configuration, users indicate their availability for emergency dispatch and their notification preferences. For example, in a school classroom setting, it may be undesirable to have audible notifications of nearby massive hemorrhages, unless they occur within the school as part of a mass casualty incident. In such cases, the tourniquet 100 can serve as a life-saving alert device by delivering an evacuation alert. The request for assistance is either accepted or denied by a user or multiple users. If denied, the request disappears, and depending on the availability of nearby tourniquets 100 or the frequency at which rejections are received more requests may be delivered. If the request is accepted, the tourniquet is deployed to stop bleeding 610. It is sometimes desirable for the centralized server 500 to send multiple requests through multiple channels, as the rate by which users respond is unpredictable. In some embodiments, the tourniquet's transmitter 206 in FIG. 2A includes a SIM card, which allows the 911 Dispatcher to talk to people present at the emergency and the patient through the speaker 142 and the user to talk back through the microphone 127 if included.

If the notification is accepted, the TQ App may open an external map site, such as Google Maps or Apple Maps, to provide navigation to the emergency coordinates. Alternatively, the User App can display an internal map 421 or 432 with directions.

Alternatively, an alert is sent to the centralized server 500 immediately upon tourniquet application 612, then delivered to the centralized server 614, causing a request for assistance to be delivered. In this case, it is less desirable to employ the User App 400 to have private tourniquets deployed to the emergency, as the bleeding has already stopped. The network then delivers a request for assistance 616 to EMS services. EMS is then either deployed 618, or in the case of a military scenario or for example in an active shooter scenario, the casualty is displaced 620. In that case it may be desirable to initiate a long-term care protocol until EMS arrives 622, which may include periodic, automatic reperfusion to restore partial blood flow to a limb to prevent long term damage from tourniquet use.

Redundancies are built into the tourniquet 100 in case of device hardware or software failure. For example, if hardware fails, the system may send additional responders to the emergency to deploy another tourniquet 100. An inflator bulb 133 such as in FIG. 1F may be used to mechanically inflate the cuff 104. In another case, the TQ Station 300 may receive the data that the tourniquet 100 has failed, and a different tourniquet 100 may be applied from the station 300. This is possible due to the tourniquet's networking capabilities.

Whereas the present disclosure has been described in relation to the drawings attached hereto, other and further modifications, apart from those shown or suggested herein, may be made within the spirit and scope of this disclosure. Those skilled in the art will appreciate that the conception, upon which this disclosure is based, may readily be utilized as a basis for the designing of other structures, methods, and systems for carrying out the several purposes of the present disclosure. That is, the present disclosure is not limited in its application to the details of construction and to the arrangements of the components set forth in the following description or illustrated in the drawings. The present disclosure is capable of other embodiments and of being practiced and carried out in various ways. Also, it is to be understood that the phraseology and terminology employed herein are for the purpose of description and should not be regarded as limiting. The descriptions of the embodiments shown in the drawings should not be construed as limiting or defining the ordinary and plain meanings of the terms of the claims unless such is explicitly indicated. The claims should be regarded as including such equivalent constructions insofar as they do not depart from the spirit and scope of the present disclosure.

We claim:

1. A networking-capable emergency tourniquet comprising:
- an adjustable and inflatable cuff configured to encircle a limb of a patient; and
- a controller unit removably coupled to the inflatable cuff, the controller unit comprising:
- a power supply;
- a microcontroller configured to control an introduction, removal, and maintenance of air within the inflatable cuff and process collected patient data;
- a communicator unit configured to communicate with a user and capable of communicating with a centralized server, the communicator unit configured to transmit a request for assistance to at least one of an emergency dispatcher and the centralized server upon activation of the power supply which activates the controller unit;
- a transmitter configured to transmit the collected patient data to the centralized server over a communication network; and
- a receiver configured to receive information from the centralized server over the communication network,
- the adjustable and inflatable cuff further comprising a limb conforming component, the limb conforming component comprising an integrated dual port air valve, the dual port air valve comprising:
- a top valve;
- at least one bottom valve; and
- a one-way check valve, wherein the integrated dual port air valve allows the adjustable and inflatable cuff to operate independently of the controller unit to maintain pressure in the adjustable and inflatable cuff even after the controller unit is detached from the adjustable and inflatable cuff.

2. The network-capable emergency tourniquet of claim 1, wherein the information from the centralized server includes at least one of visual and audible instructions to the user of the tourniquet.

3. The network-capable emergency tourniquet of claim 1, wherein the controller unit further comprises at least one of a speaker and visual display configured to deliver instructions to the user of the tourniquet.

4. The network-capable emergency tourniquet of claim 1, wherein the communicator unit is configured to transmit the collected patient data upon activation of the controller unit.

5. The network-capable emergency tourniquet of claim 1, where the collected patient data includes a location of the tourniquet and the patient.

6. The network-capable emergency tourniquet of claim 1, wherein at least one of the adjustable and inflatable cuff and the controller unit includes an RFID tag, the RFID tag configured to store information specific for the tourniquet.

7. The networking-capable emergency tourniquet of claim 1, wherein the centralized server is in communication with a plurality of network-capable emergency tourniquets.

* * * * *